US007230086B2

(12) United States Patent
Price et al.

(10) Patent No.: US 7,230,086 B2
(45) Date of Patent: Jun. 12, 2007

(54) ASSAY FOR YKL-40 AS A MARKER FOR DEGRADATION OF MAMMALIAN CONNECTIVE TISSUE MATRICES

(75) Inventors: Paul A. Price, La Jolla, CA (US); Julia S. Johansen, Frederiksberg (DK)

(73) Assignee: The Regents of the University of California, Oakland, CA (US)

(*) Notice: Subject to any disclaimer, the term of this patent is extended or adjusted under 35 U.S.C. 154(b) by 533 days.

(21) Appl. No.: 10/648,811

(22) Filed: Aug. 25, 2003

(65) Prior Publication Data
US 2005/0065325 A1 Mar. 24, 2005

Related U.S. Application Data

(63) Continuation of application No. 09/215,077, filed on Dec. 18, 1998, now Pat. No. 6,794,150, which is a continuation of application No. 08/581,527, filed as application No. PCT/US94/07754 on Jul. 8, 1994, now Pat. No. 5,935,798, and a continuation-in-part of application No. 08/089,989, filed on Jul. 9, 1993, now abandoned.

(51) Int. Cl.
C07K 16/00 (2006.01)
(52) U.S. Cl. .............................. 530/388.1; 530/387.9; 530/388.85; 530/389.7; 436/547; 436/548
(58) Field of Classification Search .................. 435/4, 435/7.1, 7.4, 7.92, 7.23, 975; 436/501, 518, 436/547, 548; 530/387.9, 388.1, 388.85, 530/389.7
See application file for complete search history.

(56) References Cited

U.S. PATENT DOCUMENTS

| 4,628,027 A | 12/1986 | Gay |
| 4,782,014 A | 11/1988 | Serban et al. |
| 5,726,061 A | 3/1998 | Robbins et al. |
| 5,773,259 A | 6/1998 | Kirkpatrick |

FOREIGN PATENT DOCUMENTS

| EP | 0398753 | 11/1990 |
| EP | 0805206 A | 11/1997 |
| EP | 0 823 478 A2 | 2/1998 |
| EP | 0 836 096 A2 | 4/1998 |
| EP | 0 823 478 A3 | 9/1999 |
| JP | 63023898 A | 2/1988 |
| WO | WO 90/08195 | 7/1990 |
| WO | WO 93/22429 | 11/1993 |
| WO | WO 95/01995 | 1/1995 |
| WO | WO 9806859 A | 2/1998 |

OTHER PUBLICATIONS

Been et al. (1986) Cell 47:207-216.
Campbell (1991) Biochemistry and Molecular Biology 23:1-114.
Gillies et al. (1989) Bio/Technology 7:799-805.
Gorman et al. (1982) Proc. Natl. Acad. Sci. 79: 6777-6781.
Hakala et al. (1993) J. Biol. Chem. 268 (34): 25803-25810.
Orslev-Petersen et al. (1986) Arthritis and Rheumatism 29 (5) 592-599.
Horslev-Petersen et al. (1988) Clin. & Exp. Rheumatology 6: 129-134.
Hu et al. (1996) J. Biol. Chem. 271 (32) 19415-19420.
Isselbacher et al. (1976) Harrison's Principles of Internal Medicine 1865-1867, 1870-1879, 1894-1896.
Johansen et al. (1992) J. Bone and Mineral Res. 7 (5): 501-512.
Johansen et al. (1992) Abstract for Scientific Conference published on or after Jul. 12, 1992.
Johansen et al. (1993) Br. J. Rheumatology 32 (11): 949-955.
Krieg et al. (1984) Nucleic Acids Res, 12 (18):7057-7071.
MacNaul et al. (1990) J. Biol. Chem. 265 (28): 17238-17245.
Mauer et al. (1980) Meth. Enzymol. 70:49-70.
Norton et al. (1985) Mol. And Cellular Biol. 5(2): 281-290.
Nyirkos et al. (1990) Biochem. J. 268:265-268.
Raz et al. (1993) Proc. Nat Acad Sci. 90 (10) 4523-4527.
Rejman et al. (1988) Biochem. Biophys Res. Comm. 150: (1) 329-334.
Renkema et al. (1995) J. Biol. Chem 270 (5) 2198-2202.
Rhode et al. (1979) Eur. J. Clin. Investigation 9:451-459.
Salacinski et al. (1981) Anal. Biochem 117:136-146.
Saxne et al. (Annal. Rheumatic Dis. 45: 491-497.
Thomas (1988) Tabers Cyclopedic Medical Dictionary 372-373.
Ulmer et al. (1992) Science 259: 1745-1749.
Ward et al. (1989) Nature 341:544-546.
Grossman et al. (1996)EMHUM2 Database Accession No. HSU58514.
Grossman et al. (1996) EMHUM2 Database Accession No. HSU58515.
(1996) EMHUM 2 Database Accession No. HSU49835.
(1996) TRHUM Database Accession No. Q15749, A15782 and Q15783.
Hørslev-Petersen et al. (1986) "Serum amino-terminal type III procollagen peptide in rheumatoid arthritis." *Arthritis and Rheumatism*, 29(5): 592-599.
EP 0 710 251 Supplementary Partial European Search Repot.
PCT.US99/22615 International Search Report.
PCT/US94/07754 International Search Report.
Cintin, C. et al. (1999) Serum YKL-40 and Colarectal Cancer. Brit. J. of Cancer 79:1494-1499.

(Continued)

*Primary Examiner*—Bao-Thuy L. Nguyen
(74) *Attorney, Agent, or Firm*—Beyer Weaver LLP; Tom Hunter

(57) ABSTRACT

The invention is a method of identifying the presence of a disease state in a mammal which is associated with degradation of connective tissue in the mammal which contains the protein known as YKL-40. The method is a competitive immunoassay for YKL-40. It can be used, for example, to identify the presence of inflammatory or degenerative joint disease and tumor metastasis (to the extent it can be correlated to serum YKL-40 levels). Serum YKL-40 levels as detected and quantified by the inventive method are also suggestive of the prognosis for the length of survival in breast cancer patients following recurrence and/or metastasis of their cancers.

4 Claims, 11 Drawing Sheets

OTHER PUBLICATIONS

Johansen et al. (1995) Serum YKL-40: A Potential Marker of Prognosis and Location of Metastases of Patients and Recurrent Breast Cancer. 32a (9):1437-1442.

Kirkpatrick et al. (1997) Induction and Expression of Human Cartilage Glycoprotein 39 and Rheumatoid Inflammatory and Peripheral Blood Monocyte-Detived Macrophages. Experimental Cell Research 237(1):46-54.

Renkema et al. (1998) Chitoriosidase, a Chitinase, and the 39-kDa Human Cartilage Glycoprotein, a Chitin-Bonding Lectin, are Homologues of Family 18 Glycolas Hydolases Secreted by Human Macrophages, EP J. Biochem. DE, Berlin, 251(251): 504-509.

Baslund et al. (1998) YKL-40 in the Circulation of Temporal Artery in Patients with Giant Cell Arteritis and Polymyalgia Rheumatica. 41.

Boot et al. (1999) Strong Induction of Members of the Chitinase Family of Proteins in Artherosclerosis: Chitotrisdase and Human Cartilagegp-39 Expresses in Lesion Macrophages. Arterioscler Thormb Vasc. Biol. 19(3)687-694.

Nordenbaek et al. (1999) YKL-40, A Matrix Protein of Specific Granules in Neutrophils, is Elevated in Serum of Proteins with Community-Aquired Pneumonia Requiring Hospitalization. J. of Infec. Dis. 180(5) 1722-1726.

Volk et al. (1998) YKL-40, A Mammalian Member of the Chitinase Family, is a Matrix Protein of Specific Granules in Human Neutrophils, Proceeding of the Association of American Physicians 110(4) 351-360.

Johansen et al., "A new Biochemical Marker for Joint Injury Analysis of YKL-40 in Serum and Synovial Fluid", British Journal of Rheumatology, 1993, 32: 949-955.

Johansen et al., "Plasma YKL-40 Concentrations in patients with Rheumatoid Arthritis", abstract for scientific conference published on or after Jul. 12, 1992.

ASSAY FOR YKL-40 AS A MARKER FOR DEGRADATION OF MAMMALIAN CONNECTIVE TISSUE MATRICES

CROSS-REFERENCE TO RELATED APPLICATIONS

This application is a continuation of U.S. Ser. No. 09/215,077, filed on Dec. 18, 1998 now U.S. Pat. No. 6,794,150, which is a continuation of U.S. Ser. No. 08/581,527, filed on Apr. 17, 1996 now U.S. Pat. No. 5,935,798, which is a 371 of PCT/US94/07754, filed on Jul. 8, 1994, which is a continuation-in-part of U.S. Ser. No. 08/089,989, filed on Jul. 9, 1993, now abandoned, which are all incorporated herein by reference in their entirety for all purposes.

STATEMENT AS TO RIGHTS TO INVENTIONS MADE UNDER FEDERALLY SPONSORED RESEARCH AND DEVELOPMENT

This invention was made in part with Government support under Grant No. AR-27029, awarded by the National Institute of Health. The Government has certain rights in this invention.

FIELD OF THE INVENTION

The invention relates to the identification of a circulating protein associated with extracellular fiber matrix metabolism in mammalian connective tissues. More specifically, it is directed to assays for the detection and quantitation of molecules and fragments of YKL-40, a protein associated with connective tissue metabolism in mammals. It also involves correlating serum levels of YKL-40 in a mammal to the presence and status of diseases in which matrix metabolism plays a role, such as joint disorders and the metastasis of certain tumors.

BACKGROUND OF THE INVENTION

The extracellular matrix of mammalian connective tissues (such as articular cartilage of joints and vascular wall tissue of the vascular and lymphatic system) provides strength to, and (to varying degrees) a barrier to the migration of cells from, the tissue. In certain disease processes, however, the matrix is degraded by hydrolytic enzymes. As the matrix degrades, the integrity of the tissue is impaired, which may allow tissue cells, by-products and other residues of the matrix metabolism to escape into bodily fluids and/or lymphatic or vascular circulation. Detection of these molecules and cells can, in certain instances, provide information regarding the biochemical characteristics of the extracellular matrix, including how it is synthesized and how it is lost. Also, where a particular molecule that is produced and/or secreted during abnormal matrix metabolism is closely related to a disease process, quantitation of that molecule in the patient's body fluids and/or tissues can help clinicians monitor the progress of the disease.

Human joint cartilage is known to contain several different types of proteins and proteoglycans, a few of which are present only in cartilage. These matrix constituents are released from cartilage tissue as it degrades during the course of certain joint diseases. The quantity of released matrix constituents (including fragments thereof and related macromolecules) present in a particular fluid or tissue may correlate with the intensity of the disease. Conversely, where the damage to the cartilage is reversible (as in secondary reactive arthritis caused by infection of the joint tissue), a reduction in levels of previously measured released matrix constituents may correlate with the degree of remission of the disease.

In practice, however, identification of reliable markers for metabolism of cartilage and other connective tissues and development of assays for their detection has proved to be a difficult task. Certain released fragments and molecules may be rapidly cleared from circulation by the lymph nodes, liver and phagocytosis (see, e.g., Frazer, et al., Hyaluronan: Sources, Turnover and Metabolism, Clinical Impact of Bone and Connective Tissue Markers 31-49 (Acad. Press, 1989); Smedsrod, "Catabolism in Liver Sinusoids", id. at 51-73; and, Heinegard, et al., Brit. J. Rheumatol., 30 (Suppl. 1): 21-24, 1991). Further, certain molecules are present in several different connective tissues, thus making correlation to metabolism in a particular tissue based on circulating levels of the molecule uncertain. Even where levels of a particular molecule can be traced to metabolism in the tissue of interest, the molecules may decline to undetectable levels or be biochemically altered in structure during those stages of a disease when a substantial quantity or connective tissue has been lost.

Not surprisingly, therefore, attempts to develop assays, especially those utilizing serum, which correlate levels of certain proteins to joint disease activity have met with mixed success. Rohde and co-workers have described radio-immunoassays (RIAs) for serum levels of amino-terminal type III procollagen peptide and its degradation products in rheumatoid arthritis (RA) patients (Rhode, et al. Eur. J. Clin. Invest, 9:451-459, 1979). This propeptide (P-III-NP) can be detected in several body fluids; a subsequent report attempted to correlate serum levels of P-III-NP to disease activity using the Rhode, et al. radioimmunoassay (H.o slashed.rslev-Petersen, et al., Arth. and Rheum., 5:592-599, 1986). While the concentrations of serum P-III-NP were significantly elevated in patients with active RA, these concentrations were also elevated to a similar degree in patient's with inactive RA, thus making the distinction between the two states based on P-III-NP levels alone difficult.

Assays of serum levels of other connective tissue metabolites and constituents in RA patients have been attempted in connection with treatment protocols to gauge the success of those protocols, again with mixed success. For example, H.o slashed.rslev-Petersen, et al., ibid, measured serum levels of P-III-NP, immunoreactive propyl 4-hydroxylase protein (1RPH), 7S domain of collagen type IV (Col IV, 7S) and fragment PI of laminin (S-Lam), which are associated with metabolism of extracellular interstitial collagens and basement membranes. Although serum levels of P-III-NP, 1RPH and Col IV, 7S were elevated in RA patients (as compared with healthy adults), the levels did not decline to normal even with apparent remission of the disease. Also, levels of S-Lam remained normal in both active and inactive RA patients. As a result, the presence and quantity of these proteins in serum does not appear to clearly correlate to the progress or remission of RA.

Similar difficulties have also prevented the identification of reliable markers for the progress of other connective tissue diseases. Identification of candidate molecules and fragments which may serve as reliable markers for connective tissue metabolism is, therefore, an important goal of clinical chemistry research. To this end, the expression of given proteins by matrix-forming cells has been assessed by immunologic assays for antigen and by hybridization assays for mRNA encoding candidate marker protein. Isolation of proteins from the extracellular matrix is, however, limited to the identification of secreted proteins that become abundant constituents of that matrix. As a result, identification of candidate proteins has been limited.

In 1992, the inventors described a method for identification of all proteins secreted by a matrix-forming cell (Johansen, et al., J. Bone and Min. Res., 7:501-512, 1992). Using this method, a 40 kD protein was identified as a secreted protein of human bone cells. The inventors hypothesized that the protein (named YKL-40 after the first three amino acids at the N-terminus and the molecular weight) could play a role in the action of Vitamin D in bone. YKL-40 appears to be the same protein identified by Rejman, et al., (Biochem. Biophys. Res. Commun., 150:329-334, 1988) as being present in mammary secretions of non-lactating cows whose mammary glands were undergoing involution As described in detail below, it has since been discovered that YKL-40 can serve as a reliable marker for joint disease, including diseases with disparate pathologies such as rheumatoid arthritis and ostecarthritis. Surprisingly, it has also been discovered that serum levels of YKL-40 are also substantially elevated in patients with metastasis of breast cancer cells, particularly those patients who survive for a relatively short period of time following recurrence and metastasis of their cancer. Further, the inventors have determined that significantly elevated levels of YKL-40 appear in the sera of persons having connective tissue degradation in organs such as the liver and prostate.

The methods for detecting and quantifying levels of YKL-40 in biological samples described herein, therefore, provide a means of charting the progress of not only joint disease, but also cancer cell metastasis. Further, based on the apparent relationship of serum levels of YKL-40 to connective tissue metabolism, it can be reasonably predicted that the methods described will be of use in the diagnosis and monitoring of other diseases in which connective tissue metabolism plays a role, such as osteoporosis.

SUMMARY OF THE INVENTION

Detection and quantitation of a marker for diseases whose activity can be correlated to loss and/or synthesis of connective tissue matrices can be of value in diagnosing and monitoring the progress of both the disease and its amelioration. One such marker is YKL-40, a protein of about 40 kD molecular weight which has been found in elevated concentrations in the blood and synovial fluid of human patients with joint disease, as well as in the blood of human patients with breast cancer or disorders of organs such as the liver.

A point of commonality between these conditions is their relationship to connective tissue loss. Specifically, connective tissue loss in joint disease results from its degradation by enzymes released in the disease process. In cancer cell metastasis, it is believed that degradation of the connective tissue of vessel walls and, possibly, of body organs permits migration of cells from the primary cancer tissue. Similarly, with the loss of organ tissue in an organ degenerative disease such as cirrhosis, it can be expected that connective tissue within the organ may also be degraded.

An object of the invention, therefore, is to provide a method of detecting and quantifying YKL-40 in biological samples using an antibody specific for YKL-40 and, where appropriate, a detectably labeled antigen (YKL-40).

Another object of the invention is to provide methods for diagnosis of diseases which are correlated to the loss and/or synthesis of connective tissue as indicated by levels of YKL-40 detected in a biological sample. In this respect, the invention is expected to be of particular use in the diagnosis of joint disease (such as RA), cancer cell metastasis (as in, for example, breast cancer), diseases related to loss of connective tissue in bone (such as osteoporosis and osteoarthritis), and diseases related to loss of connective and/or other tissue in organs (such as cirrhosis of the liver).

Another object of the invention is to provide methods for the quantitation of levels of YKL-40 to monitor the progress and/or amelioration of a disease which is associated with connective tissue metabolism related to the presence of YKL-40. Again, the invention is expected to be of particular use in tracking the progress and/or amelioration of joint disease (such as RA), of cancer cell metastasis (as in, for example, breast cancer), diseases related to the loss of connective tissue in bone such as osteoporosis and osteoarthritis, and diseases that result in the loss of connective tissue in organs, such as cirrhosis of the liver.

DETAILED DESCRIPTION OF THE INVENTION

A. Definitions

Figure 1:
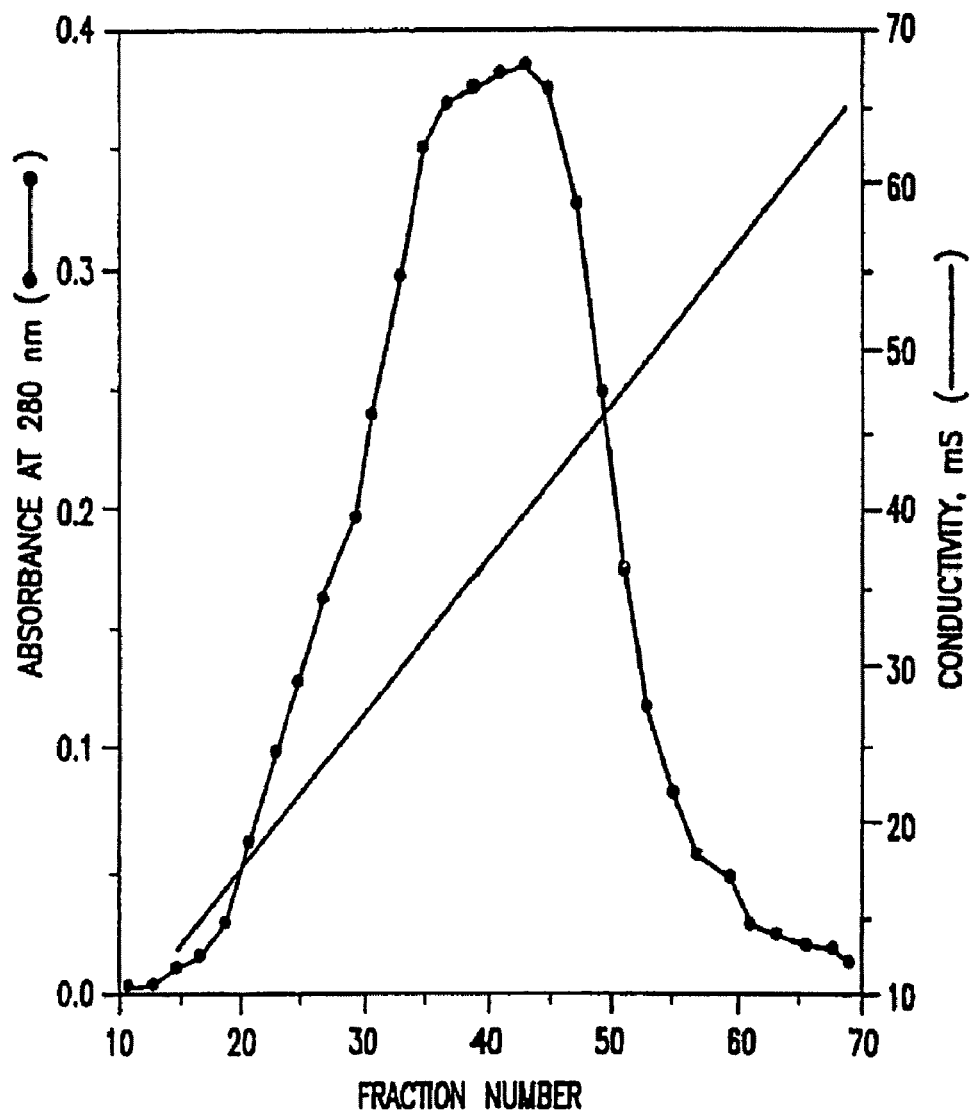
FIG. 1 shows the elution position of substantially pure serum YKL-40 on a gel filtration column.

The following definitions are provided to simplify discussion of the invention. They should not, therefore, be construed as limiting the invention, which is defined in scope by the appended claims.

"Antibody" includes intact molecules as well as fragments thereof such as Fab and F(ab')$_2$ which are capable of binding an epitopic determinant on the YKL-40 protein.

"Antigen" (as used in the context of the inventive assay) refers to the YKL-40 protein. The N-terminal amino acid sequence of this protein is set forth in the sequence listing herein as SEQ ID. NO: 1.

"Mammal" as used herein includes both humans and non-humans.

"mAb" refers to a monoclonal antibody.

"Substantially pure", as used to describe YKL-40, refers to the substantially intact molecule which is essentially free of other molecules with which YKL-40 may be found in nature.

"Disease state" refers to an illness or injury in a mammal.

"Associated" with respect to the role in YKL-40 in a disease state in a mammal refers to release of YKL-40 into a tissue or fluid of the mammal which release occurs during or at the onset of the disease state and is the result of the onset or occurrence of the disease state.

"Ameliorate" refers to a lessening in the severity of a disease state, including remission or cure thereof.

B. Isolation and Purification of YKL-40.

To develop antibodies for use in all assay procedures and antigen for use in competitive assay procedures according to the methods of the invention, YKL-40 must be obtained from a biological sample or synthesized, preferably in a substantially pure form. Native YKL-40 may be obtained from any mammalian fluid or tissue in which it is known to be present. Although the normal distribution of YKL-40 in mammals is as yet not completely known, it has been found in serum, synovial fluid and conditioned media of chondrocytes and osteosarcoma cells (MG63 cell line, American Type Culture Collection, Rockville, Md. ["ATCC"]). Northern blot analyses have shown that YKL-40 mRNA is expressed at high levels in the liver, weakly by brain, kidney and placenta, and at undetectable levels by heart, lung, and skelatal muscle (Hakala, et al. (1993) J. Biol. Chem, 268: 25803-25810).

Condition media can be prepared by culturing YKL-40 producing cells according to means known in the art, preferably using RPMI 1640 serum-free media (Irvine Scientific, Irvine, Calif.). YKL-40 is purified according to means known in the art, such as by affinity chromatography or gel filtration (on, for example, the resin SEPHACRYL S-200-HR from Pharmacia, Piscataway, N.J.). YKL-40 has a molecular weight of about 40 kD. The N-terminal amino acid sequence is shown in the sequence listing as SEQ ID. NO. 1; the full coding region of the gene for YKL-40 is contained in SEQ ID NO:4. Substantial homology along the N-terminal and internal amino sequences (the latter of which are shown in SEQ ID NO. 2, ("YKL-40 peptide A") and SEQ. ID. NO:3, ("YKL-40 peptide B")) with a bacterial polysaccharide hydrolase (chitinase) supports the conclusion that YKL-40 degrades polysaccharide components in connective tissue. Specifically, SEQ ID. NO. 2 correlates to 14/19 residues of an internal amino acid sequence for chitinase, while about 50% of the residues in the N-terminal sequence for YKL-40 correlate to the N-terminus of chitinase (SEQ. ID. NO. 3). YKL-40 also has substantial sequence identity to a protein secreted by activated murine macrophages (PIR Accession No. S27879). Allowing for some gaps in sequence alignment, there are 142 identities between residues 26 to 359 of the complete 383 residue sequence of YKL-40 (GenBank Accession No. M80927; see, SEQ ID NO:4), and residues 27-369 of the 505 residue macrophage secretory protein.

Although it is not intended that the invention be limited by a particular theory regarding the mechanism by which YKL-40 functions in a given disease state, such sequence identities strongly suggest that YKL-40 is an enzyme that hydrolyzes glycosidic bonds in an as yet unidentified macromolecule in the extracellular environment of cells. Since chitin itself is not found in vertebrates, and since YKL-40 apparently does not possess chitinase activity, it is probable that divergent evolution of in ancestral chitinase altered the specificity of the vertebrate enzyme so that it now cleaves a different glycosidic linkage than the one targeted by chitinase.

In healthy connective tissue, YKL-40 may play a role in normal tissue remodeling. Given the substantial increase in YKL-40 detected as described below in the sera and synovial fluid of persons afflicted with connective tissue degradative diseases, and the apparent absence of YKL-40 in healthy cells, it is believed that the production and/or secretion of YKL-40 in diseases associated with YKL-40 is upregulated to an abnormal level through an as yet unknown disease process. Thus, it is likely, that YKL-40 is a cellular product which plays an active role in the disease process rather than merely a structural component of degraded connective tissue. For ease of reference, therefore, connective tissue on which secreted YKL-40 acts or in which it is secreted will be referred to herein as connective tissue "containing" YKL-40.

For use in the inventive assay, YKL-40 and immunogenic fragments thereof may also be synthesized according to means which are well-known in the art. Using conventional techniques, the full-length gene can be expressed using suitable expression vectors known in the art or the peptide can be chemically constructed using amino acids corresponding to the deduced amino acid sequence for YKL-40.

For example, YKL-40 may be synthesized without undue experimentation by commonly used methods such as t-BOC or FMOC protection of alpha-amino groups. Both methods involve stepwise synthesis whereby a single amino acid is added at each step starting from the C terminus of the peptide (see, Coligan, et al., Current Protocols in Immunology, Wiley Interscience, 991, Unit 9). Peptides of the invention can also be synthesized by various well known solid phase peptide synthesis methods, such as those described by Merrifield, J. Am. Chem. Soc., 85:2149 (1962), and Stewart and Young, Solid Phase Peptides Synthesis, (Freeman, San Francisco, 27-62, 1969), using a copoly(styrene-divinylbenzene) containing 0.1-1.0 mMol amines/g polymer.

In this latter method, upon completion of chemical synthesis, the peptides can be deprotected and cleaved from the polymer by treatment with liquid HF-10% anisole for about ¼-1 hours at 0.degree. C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

DNA sequences for use in producing YKL-40 and YKL-40 peptides can also be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions (Maniatis, Molecular Cloning: A Laboratory Manual, Cold Spring Harbor, 1984) directed to avoid non-specific binding, it is possible, for example, to allow the autoradiographic visualization of a specific cDNA clone by the hybridization of the target DNA to that single probe in the mixture.

A YKL-40 containing cDNA library can be screened by injecting the various mRNA derived from cDNAs into oocytes, allowing sufficient time for expression of the cDNA gene products to occur, and testing for the presence of the desired cDNA expression product, for example, by using antibody specific for YKL-40 or by using probes for the repeat motifs and a tissue expression pattern characteristic of YKL-40. Alternatively, a cDNA library can be screened indirectly for YKL-40 peptides having at least one epitope using antibodies specific for the polypeptides. As described in Section C below, such antibodies can be either polyclonally or monoclonally derived and used to detect expression product indicative of the presence of YKL-40 cDNA (see SEQ ID NO:4).

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. The development of specific DNA sequences encoding YKL-40 or fragments thereof, can also be obtained by: 1) isolation of double-stranded DNA sequences from the genomic DNA, and 2) chemical manufacture of a DNA sequence to provide the necessary codons for the polypeptide of interest.

The gene encoding YKL-40 may be inserted into a recombinant expression vector. The term "recombinant expression vector" refers to a plasmid, virus or other vehicle known in the art that has been manipulated by insertion or incorporation of the appropriate genetic sequences. Such expression vectors contain a promoter sequence which facilitates the efficient transcription of the inserted genetic sequence of the host.

Transformation of a host cell with recombinant DNA may also be carried out by conventional techniques as are well known to those skilled in the art. Where the host is prokaryotic, such as E. coli, competent cells which are capable of DNA uptake can be prepared from cells harvested after exponential growth phase and subsequently treated by the CaCl.sub.2 method by procedures well known in the art. Alternatively, MgCl.sub.2 or RbCl can be used. Transformation can also be performed after forming a protoplasm to the host cell or by electroporation.

Isolation and purification of microbially expressed polypeptide, or fragments thereof, provided by the invention, may be carried out by conventional means including preparative chromatography and immunological separations involving monoclonal or polyclonal antibodies.

Peptides and polynucleotides of the invention include functional derivatives of YKL-40, YKL-40 peptides and nucleotides encoding therefor. By "functional derivative" is meant the "fragments," "variants," "analogs," or "chemical derivatives" of a molecule. A "fragment" of a molecule, such as any of the DNA sequences of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical.

Further, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th Ed., Mack Publishing Co., Easton, Pa., 1980.

Minor modifications of the YKL-40 primary amino acid sequence may result in proteins and peptides that have substantially similar activity as compared to the YKL-40 peptides described herein. Such modifications may be deliberate, as by site-directed mutagenesis, or may be spontaneous. All of the peptides produced by these modifications are included herein as long as the biological activity of YKL-40 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which may not be required for the enzyme to exert the desired catalytic or antigenic activity.

C. Antibodies to YKL-40.

Either polyclonal or monoclonal antibodies may be used in the immunoassays and therapeutic methods of the invention described below. Polyclonal antibodies may be raised by multiple subcutaneous or intramuscular injections of substantially pure YKL-40 or antigenic YKL-40 peptides into a suitable non-human mammal. The antigenicity of YKL-40 peptides can be determined by conventional techniques to determine the magnitude of the antibody response of an animal which has been immunized with the peptide. Generally, the YKL-40 peptides which are used to raise the anti-YKL-40 antibodies should generally be those which induce production of high titers of antibody with relatively high affinity for YKL-40.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because YKL-40 may be conserved among mammalian species, use of a carrier protein to enhance the immunogenecity of YKL-40 proteins is preferred.

The antibodies are then obtained from blood samples taken from the mammal. The techniques used to develop polyclonal antibodies are known in the art see, e.g., Methods of Enzymology, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies See, for example, Coligan, et al., Unit 9, Current Protocols in Immunology, Wiley Interscience, 1991).

Preferably, however, the YKL-40 antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and F(ab').sub.2, which are capable of binding an epitopic determinant. Also, in this context, the term "mAb's of the invention" refers to monoclonal antibodies with specificity for YKL-40.

The general method used for production of hybridomas secreting mAbs is well known (Kohler and Milstein, Nature, 256:495, 1975). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines.

Confirmation of YKL-40 specificity among mAb's can be accomplished using relatively routine screening techniques (such as the enzyme-linked immunosorbent assay, or "ELISA") to determine the elementary reaction pattern of the mAb of interest.

It is also possible to evaluate an mAb to determine whether it has the same specificity as a mAb of the invention without undue experimentation by determining whether the mAb being tested prevents a mAb of the invention from binding to YKL-40 isolated as described above, if the mAb being tested competes with the mAb of the invention, as shown by a decrease in binding by the mAb of the invention, then it is likely that the two monoclonal antibodies bind to the same or a closely related epitope.

Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

D. Immunoassay Procedures.

The immunoassay procedure used must be quantitative so that levels of YKL-40 in a patient with disease may be distinguished from normal levels which may be present in healthy humans and/or background levels measured in the patient. Competitive and sandwich assays on a solid phase using detectible labels (direct or indirect) are, therefore, preferred. The label will provide a detectible signal indicative of binding of antibody to the YKL-40 antigen. The antibody or antigen may be labelled with any label known in the art to provide a detectible signal, including radioisotopes, enzymes, fluorescent molecules, chemiluminescent molecules, bioluminescent molecules and colloidal gold. Of the known assay procedures, radioimmunoassay (RIA) is most preferred for its sensitivity. A radioisotope will, therefore, be the preferred label.

Examples of metallic ions which can be directly bound to an antibody, or indirectly bound to the YKL-40 antigen are well-known to those of ordinary skill in the art and include $^{125}$I, $^{111}$In, $^{97}$Ru, $^{67}$Ga, $^{68}$Ga, $^{72}$As, $^{89}$Zr, $^{90}$Y and $^{201}$Tl. Preferred for its ease of attachment without compromise of antigen binding specificity is $^{125}$I (sodium salt, Amersham, United Kingdom). Labelling of YKL-40 with $^{125}$I may be performed according to the method described in Salacinski, et al., Anal. Biochem., 117:136-146, 1981. Iodogen for use to provide the $^{125}$I label (1,3,4,6-tetrachloro- 3.alpha., 6.alpha.-diphenyl glycoluril) is commercially available from Pierce and Warriner, Chester, England.

The radioimmunoassay of the invention uses standards or samples incubated with a substantially equal volume of YKL-40 antiserum and of YKL-40 tracer. Standards and samples are generally assayed in duplicate. The sensitivity (detection limit) of the assay of the invention is about 10 μg/L. Sensitivity in this context is defined as the detectible mass equivalent to twice the standard deviation of the zero binding values. The standard curve will generally be linear between 20 and 100 μg/L The intra- and interassay coefficients of variance for the assay described in the following examples are <6.5% and <12%, respectively.

It will be appreciated by those skilled in the art that, although not necessarily as sensitive as an RIA, assay procedures using labels other than radioisotopes have certain advantages and may, therefore, be employed as alternatives to the preferred RIA format. For example, an enzyme-linked immunosorbent assay (ELISA) may be readily automated using an ELISA microtiter plate reader and reagents which are readily available in many research and clinical laboratories. Fluorescent, chemiluminescent and bioluminescent labels have the advantage of being visually detectible, though they are not as useful as radioisotopes to quantify the amount of antigen bound by antibody in the assay.

Further, it will be appreciated by those of skill in the art that means other than immunoassays may be employed to detect and quantify the presence of YKL-40 in a biological sample. For example, a polynucleotide encoding YKL-40 may be detected using quantitative polymerase chain reaction (PCR) protocols known in the art. The preferred method for performance of quantitative PCR is a competitive PCR technique performed using a competitor template containing an induced mutation of one or more base pairs which results in the competitor differing in sequence or size from the target YKL-40 gene template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions.

Once the aminated or biotinylated strands of the PCR products are immobilized, the unbound complementary strands are separated in an alkaline denaturing wash and removed from the reaction environment. Sequence-specific oligonucleotides ("SSO's") corresponding to the target and competitor nucleic acids are labelled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates. This method is advantageous in that it is quantitative, does not depend upon the number of PCR cycles, and is not influenced by competition between the SSO probe and the complementary strand in the PCR product.

Alternatively, part of the polymerization step and all of the hybridization step can be performed on a solid phase support. In this method, it is an nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above.

A target to competitor nucleic acid ratio can be determined by detection of labelled oligonucleotide SSO probes using appropriate measurement means (preferably ELISA readers) and standard curve as described supra. The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

Molecules capable of providing different, detectible signals indicative of the formation of bound PCR products known to those skilled in the art (such as labelled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional non-competitive PCR protocol.

Those of ordinary skill in the art will know, or may readily ascertain, how to select suitable primers for use in the above methods. For further details regarding the above-described techniques, reference may be made to the disclosures in Kohsaka, et al., Nuc. Acids Res., 21:3469-3472, 1993; Bunn, et al., U.S. Pat. No. 5,213,961; and to Innis, et al., PCR Protocols: A Guide to Methods and Applications, Acad. Press, 1990, the disclosures of which are incorporated herein solely for purposes of illustrating the state of the art regarding quanititative PCR protocols.

E. Diagnostic Application.

As shown in examples provided below, diagnosis of disease based on measured levels of YKL-40 can be made by comparison to levels measured in a disease-free control group or background levels measured in a particular patient. The diagnosis can be confirmed by correlation of the assay results with other signs of disease known to those skilled in the clinical arts, such as the diagnostic standards for RA and breast cancer described in the examples below.

Where the amelioration of a disease (such as RA) can be related to reduction in levels of YKL-40 (and concomitant cartilage repair), YKL-40 levels in a biological assay sample taken from the patient (e.g., synovial fluid) should be measured before (for background) and periodically during the course of treatment. Because reductions in YKL-40 levels may be transient, the assay will preferably be performed at regular intervals (e.g., every 4 weeks) closely before and after each treatment. Depending on the course of treatment, tumor load and other clinical variables, clinicians of ordinary skill in the art will be able to determine an appropriate schedule for performing the assay for diagnostic or disease/treatment monitoring purposes.

Because in certain instances serum YKL-40 may stem from sources other than the tissue of interest, a sample should, if possible, be taken from the tissue of interest. For example, for diagnosis or monitoring of joint disease the assay sample will preferably be drawn from the synovial fluid of the affected or potentially affected joint. For diagnosis and monitoring of tumor metastasis, however, the preferred source for the assay sample will be blood. Those of ordinary skill in the art will be able to readily determine which assay sample source is most appropriate for use in diagnosis of a particular disease for which YKL-40 is a marker.

The levels of YKL-40 which are indicative of the development or amelioration of a particular disease will vary by disease and, to a lesser extent, by patient. Generally, however, as demonstrated by the data presented in the Examples, the median concentration of YKL-40 detected in sera from a sample group of 736 children and adults was 80 µg/l in children (aged 6-17 years) and 102 µg/l in adults (aged 20-79 years). No statistically significant variations between these values were observed between different age groups of children or adults younger than 69 years. Adults older than 69 years, however, tended toward higher serum YKL-40 levels than were present in the sera of adults younger than 69 years. Thus, for purposes of diagnosing the onset, progression, or amelioration of disease, variations in the levels of YKL-40 of interest will be those which differ on a statistically significant level from the normal (i.e., healthy) population and which correlate to other clinical signs of disease occurrence and/or amelioration known to those skilled in the clinical art pertaining to the disease of interest (i.e. "diagnostically significant levels" of YKL-40).

For example, in inflammatory joint diseases synovial fluid YKL-40 levels can be correlated to other biochemical markers of joint disease, in particular elastolytic activity by monocytes and macrophages for the degradation of proteoglycans and collagens in synovial fluid. YKL-40 levels also correlate well to elevated IL-6 levels in synovial fluid. IL-6 is secreted by chondrocytes and synovial cells and serves to regulate immune responses, including inflammation. Relatively high levels of IL-6 are found in the synovial fluid of patients with inflammatory and degenerative arthropathies.

Correlation also exists to a somewhat lesser extent between YKL-40 levels and acute C-reactive protein (CRP) levels. CRP is present in elevated quantities in the acute phase of rheumatic joint diseases and appears to play a biologic role in inflammation. YKL-40 levels similarly correlate with serum P-III-NP levels, which reflect local inflammatory alterations in type III collagen metabolism in synovial fluid. Although it is not intended that the invention be limited to a particular diagnosis, the correlation of YKL-40 levels suggests that its levels may in particular be indicative of inflammation in joint disease. Of course, any diagnosis indicated by YKL-40 measurements made according to the methods of the invention will be independently confirmed with reference to clinical manifestations of disease known to practitioners of ordinary skill in the clinical arts.

By way of further example, in breast cancer patients, serum YKL-40 levels are elevated in patients with cancer cell metastasis as compared to patients without breast cancer. It is probable that the elevated levels of YKL-40 in serum are produced at least in part by degeneration of the connective barrier to the entrance of cancer cells into blood. It can be expected that a similar process may accompany entrance of cancer cells into lymphatic circulation. As demonstrated by the data presented below, the detected elevations in serum YKL-40 appear to be indicative of metastasis to viscera and bone, rather than to localised sites, skin or solitary lymph glands. However, the latter metastases may be detected fairly readily by conventional medical examination.

Further, greatly elevated levels of YKL-40 appear in the sera of patients who have experienced a metastatic recurrence of breast cancer (in particular, with metastasis to bone and/or viscera). As compared to a median concentration of serum YKL-40 in age-matched controls (about 102 µg/1), patients with confirmed metastases to bone (the most common site of breast cancer cell metastasis) had a median concentration of serum YKL-40 of about 328 µg/l. Further, patients with confirmed metastases to viscera had a median concentration of serum YKL-40 of about 157 µg/l.

In contrast, markers now in common use for bone metastases (serum total alkaline phosphatase, bone alkaline phophatase and bone Gla protein) show considerable variation in patients with metastatic breast cancer; increases in serum bone Gla protein in particular have not been shown to be diagnostic for breast cancer metastasis to bone.

Interestingly, elevation of serum levels of YKL-40 correlate to the number of months each patient can be expected to survive following recurrence of the cancer, particularly in those patients having serum YKL-40 levels equal to or greater than about 164 µg/l, most particularly in those patients having serum YKL-40 levels equal to or greater than about 207 µg/l (i.e., "prognostically significant levels" of YKL-40). Generally, the higher the level of YKL-40, the shorter the period of survival.

F. Drug Screening Application

As discussed above, YKL-40 appears to be a hydrolytic enzyme whose production is increased during the course of a disease state associated with the degeneration of connective tissue. In particular, it appears that YKL-40 is involved in the digestion of connective tissue that causes the loss of such tissue when it is digested more rapidly than it is repaired. Logically, therefore, agents that inhibit the production and/or activity of YKL-40 would be expected to limit connective tissue loss.

To that end, the YKL-40 protein, peptides and antibodies of the invention will be useful in screening potential inhibitors of YKL-40. Potential inhibitors of YKL-40 activity include substrate molecules that will competitively bind to YKL-40 and antibodies specific for YKL-40. For example, potential YKL-40 substrate molecules may be screened and identified using the substantially pure YKL-40 of the invention in a competitive immunoassay with YKL-40 antibodies. Those of skill in the art will recognize, however, that substrate molecule binding to YKL-40 may also be characterized by determination of other parameters, such as binding kinetics and affinity.

Once a molecule has been determined to bind YKL-40, other potential substrate molecules may be screened for binding by inhibition and/or competitive binding studies as described supra with respect to screening of mAb's with specificity for YKL-40.

G. Therapeutic Application

Assuming the accuracy of the above prediction of YKL-40 enzyme activity, it can be expected that YKL-40 substrate molecule and anti-YKL-40 antibody compositions will have therapeutic efficacy. More specifically, it is expected that YKL-40 activity can be attenuated (thus reducing the host's response to response to YKL-40; e.g. digestion of connective tissue) by blocking binding of native YKL-40 substrate to YKL-40 with anti-YKL-40 antibodies and/or by competitive binding of YKL-40 to pharmaceutically acceptable substrate molecules.

To that end, YKL-40 substrate molecule or anti-YKL-40 compositions are prepared for administration by mixing YKL-40 substrate molecules having the desired degree of purity, or anti-YKL-40 antibodies having the desired degree of affinity for YKL-40, with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. Such compositions may also be lyophilized and will be pharmaceutically acceptable; i.e., suitably prepared and approved for use in the desired application.

For treatment of joint disease and degenerative organ disease (e.g., cirrohsis of the liver), YKL-40 activity will preferably be targeted in the joint or organ rather than systemically. Routes of administration for the joint or organ of interest (e.g., injection, catheterization) are known to those of ordinary skill in the clinical arts. Alternatively, administration may be by any enternal or parenteral route in dosages which will be varied by the skilled clinician depending an the patient's presenting condition and the therapeutic ends to be achieved.

The level of YKL-40 activity and/or production may be monitored by the assay described hereinabove as well as by reference to a reduction in clinical manifestations of connective tissue loss associated with the disease state to be treated. A dosage which achieves this result will be considered a "therapeutically effective" dosage. Generally, however, dosages of the YKL-40 substrate molecule will vary from about 10 units/m.sup.2 to 20,000 units/m.sup.2, preferably from about 5000 to 6000 units/m.sup.2, in one or more dose administrations weekly, for one or several days.

H. Kits for Use in Therapeutic and Diagnostic Applications.

For use in the diagnostic research and therapeutic applications suggested above, kits are also provided by the invention. In the diagnostic and research applications such kits may include any or all of the following: assay reagents, buffers, YKL-40 protein and/or fragments, YKL-40 recombinant expression vectors, YKL-40 oligonucleotides and other hybridization probes and/or primers, YKL-40 substrate molecules and/or a suitable assay device. A therapeutic product may include sterile saline or another pharmaceutically acceptable emulsion and suspension base for use in reconstituting lyophilized YKL-40 substrate molecules or anti-YKL-40 suspensions, suitably labeled and approved containers of YKL-40 substrate molecules or anti-YKL-40 compositions, and kits containing these products for use in connection with the diagnostic kit components as described above.

Examples illustrating the correlation of YKL-40 levels to joint disease activity, progress of treatment for joint disease, organ degradation, cancer cell metastasis and cancer survival rates are provided below. These examples should not, however, be considered to limit the scope of the invention, which is defined by the appended claims.

In the examples, the abbreviation "min." refers to minutes, "hrs" and "h" refer to hours, and measurement units (such as "ml") are referred to by standard abbreviations.

EXAMPLE I

Isolation and Purification of YKL-40 from Human Osteosarcoma Cell Line MG63

YKL-40 was purified from serum-free conditioned medium of the human osteosarcoma cell line MG63 (MG63 cells were obtained from the American Type Culture Collection, Rockville, Md.). Cells were cultured in 100 mm dishes with RPMI 1640 medium containing 10% newborn calf serum, 100 Units/ml penicillin, 100 µg/ml streptomycin, 50 µg/ml vitamin C, and 1 µg/ml vitamin K.sub.1. The cultures were incubated at 37.degree. C. in a humidified atmosphere of 10% CO.sub.2. When the cells reached confluence, the culture medium was removed and the cell layer was washed twice with 10 milliliters (ml) of phosphate buffered saline.

Ten mls of serum-free RPMI 1640 media containing 50 µg/ml vitamin C and 1 µg/ml vitamin $K_1$ was then added to each dish. 48 hours later, conditioned medium was decanted from each dish and replaced with 10 ml of fresh serum-free medium containing the same level of added constituents. This procedure was repeated every 48 hours for up to 10 days. Conditioned medium was freed of cells and debris by centrifugation and stored at −20° C. until use.

YKL-40 was purified by a modification of the heparin-affinity chromatography method described in Nyirkos, et al., (1990) *Biochem. J.*, 269:265-268. Specifically, YKL-40 was first concentrated from 4.75 L of conditioned medium by adsorption of 40 ml (packed volume) of HEPARIN-SEPHAROSE CL-68 resin (from Pharmacia) by stirring or 2 hours at room temperature. The resin was then placed into a 2.times.24 cm column and washed with 3 column volumes of 0.01 Molar sodium phosphate buffer (pH 7.4) containing 0.05 M NaCl. YKL-40 was eluted from the resin at room temperature by a linear gradient from 0.05 to 1.2 M NaCl in 0.01 Molar sodium phosphate buffer pH 7.4 (200 ml each condition).

To characterize the purity of YKL-40, 5 µl from every third fraction of the peak fractions from the HEPARIN-SEPHAROSE CL-6B affinity chromatography procedure described were combined with 25 µl SDS loading buffer electrophoresed on a 5-20% SDS-polyacrylamide gradient gel (BioRad, Laboratories, Richmond, Calif.), and stained with Coomassie brilliant blue. The concentration of the final YKL-40 used for standard and tracer in the inventive assay is based on an absorbance of 1.44 for a 1 milligram (mg) per ml solution of YKL-40.

Articular cartilage was obtained from the knees of cadavers within 18 hours of death and of a patient undergoing joint replacement for osteoarthritis, and chondrocytes were isolated by sequential enzymatic digestion according to methods known in the art (see, e.g., Guerne, et al. (1990) *J. Immun.*, 144:499-505). The resulting cells were a homogenous population of chondrocytes, since only the superficial layers of cartilage were used for isolation of the cells and, in contrast to fibroblasts or synoviocytes, the cells were nonadherent. The cells were cultured in DMEM-high glucose medium supplemented with 10% fetal calf serum, 100 Units/ml of penicillin, 100 µg/ml streptomycin, and 50 µg/ml vitamin C (Irvine Scientific, Irvine, Calif.). Cells were grown in 175 cm.sup.2 tissue culture flasks (primary cultures) or in 100 mm dishes (later passages) in a humidified atmosphere of 10% $CO_2$ at 37° C. The cells were subcultured at a 1:3 ratio after trypsinization of confluent monolayers. To obtain conditioned medium for analysis, the culture medium was removed after the cells reached confluence and the cell layer was washed twice with 30 ml (175 cm.sup.2 flasks) or 10 ml (100 mm dishes) of phosphate buffered saline (PBS). The same volume of serum-free DMEM-high glucose medium containing antibiotics, and 50 μg/ml vitamin C was then added to each culture. Conditioned medium was removed after 48 hours and replaced with the same volume of fresh serum-free medium. This procedure was repeated every 48 hours for up to 14 days. Conditioned medium was freed of cells and debris by centrifugation for 5 minutes at 1600 g and frozen at −20° C. until use.

EXAMPLE II

Preparation of Assay Samples for Radioimmunoassay

1. Assay Sample Sources

Assay samples were obtained from the sera of 49 patients with inflammatory or degenerative joint diseases (34 women and 15 men, aged 23-80 years with a median age of 65 years). 29 patients had RA, 7 had osteoarthritis, 4 had crystal arthritis, 2 had psoriatic arthritis, 5 had reactive arthritis and 2 had monoarthritis. Diagnoses were based on the criteria described in Arnett, et al. (1988) Arthritis Rheum. 31: 315-324 (American Rheumatism Association Standards), clinical and radiographic examinations of the knees, and direct microscopy of synovial fluid. The patients had a serum CRP level of 25-1600 (median 165). 34 patients were taking non-steroidal anti-inflammatory drugs and 17 were receiving slow acting antirheumatic agents. 15 patients had received glucocorticoid therapy systemically or locally within the past 3 months. The inflammation of the knee was evaluated by a clinical index rating from 0-6, consisting of palpable synovial swelling (range 0-3) and pain on palpation (0-3).

2. Collection of Serum and Synovial Fluid

Blood samples were allowed to clot at room temperature and then centrifuged at 1500 g for 10 minutes. Knee joint aspirations were performed using conventional aseptic technique without local anesthesia. The synovial fluid was withdrawn from each subject as completely as possible using a 1.2-mm-gauge needle, and collected in sterile tubes containing ethylene-diamine-tetracetate (EDTA, 5 mM final concentration). The synovial fluid samples were centrifuged at 1800 g for 30 minutes in order to remove any extraneous debris. The samples were either analyzed immediately or stored at −80° C. for later analysis.

EXAMPLE III

Preparation of Labelled Antigen and Antibodies for Radioimmunoassay for YKL-40

1. Preparation of Radioiodinated YKL-40

Purified YKL-40 was labelled with $^{125}$I (sodium salt, Amersham, UK) according to the Iodogen method referenced supra. Specifically, 10 μg YKL-40 was incubated for 10 minutes with 18.5 MBq $^{125}$I using 2 μg of iodogen (Pierce and Warriner, Chester, England, UK) as oxidant in a reaction volume of 110 μl. Iodination was terminated by moving the reaction mixture from the iodogen tube. The labelled YKL-40 was separated from free iodine by gel filtration using a SEPHADEX G-25 column (1.times.12.5 cm, from Pharmacia) equilibrated with assay buffer (16 mM sodium phosphate buffer pH 7.4, 0.12 M NaCl, 0.1% (w/v) human serum albumin). The calculated specific activity of the labeled was about 15 Ci/g. The elution position of YKL-40 (purified) and of YKL-40 taken from the serum of a patient with RA is shown in FIG. 1.

2. Preparation of Antibodies

New Zealand white rabbits were immunized by monthly multiple site subcutaneous or intramuscular injection of purified YKL-40. Each injection was made with 0.5 mg of human YKL-40 emulsified in incomplete Freund's adjuvant (1:1). The first 4 injections were given at intervals of two weeks and rabbits were bled 10-12 days after the fourth injection. Injections were thereafter given at 4 week intervals and the animals were bled 10-12 days after each injection. Crossed immunoelectrophoresis showed that the antibodies were monospecific for YKL-40.

It will be understood by those skilled in the art that the radioisotopic label could be attached to the antibodies described above rather than the antigen with functional equivalence in the assay claimed.

EXAMPLE IV

Radioimmunoassay for YKL-40 to Detect YKL-40 Levels in Serum and Synovia of Patients with Rheumatoid Arthritis or Other Joint Disease The assay samples described in Example II were assayed as follows. YKL-40 antibodies, standards and the tracer were diluted in assay buffer. In the assay 100 μl of standards or samples were incubated with 100 μl of YKL-40 antiserum (1:10,000) and 100 μl of YKL-40 tracer (about 15,000 counts/minute) in a final volume of 400 μl at room temperature for 20-24 hours. The antibody-bound tracer was then separated by incubation with 100 μl of SAC-CEL (donkey anti-rabbit antibody coated cellulose suspension; Wellcome Diagnostics Ltd, UK) at room temperature for 30 minutes. After addition of 1 ml of distilled water the tubes were centrifuged at 2000 g for 10 minutes, the supernatant decanted, and the radioactivity of the precipitate counted in an automatic gamma counter (LKB Wallace, CLINI-GAMMA 1272) for the time of 10,000 counts.

The precision (intra-assay variation) was calculated from replicate determinations (20 times) on each of three quality control sera in a single assay. The reproducibility (inter-assay variation) was calculated from data obtained during a 5 month period (20 assays) on each of three quality control sera. YKL-40 concentrations in corresponding serum and EDTA plasma samples were compared in 75 blood donors.

All standards and samples were assayed in duplicate. The standard curve was constructed by use of a spline function.

Figure 2:
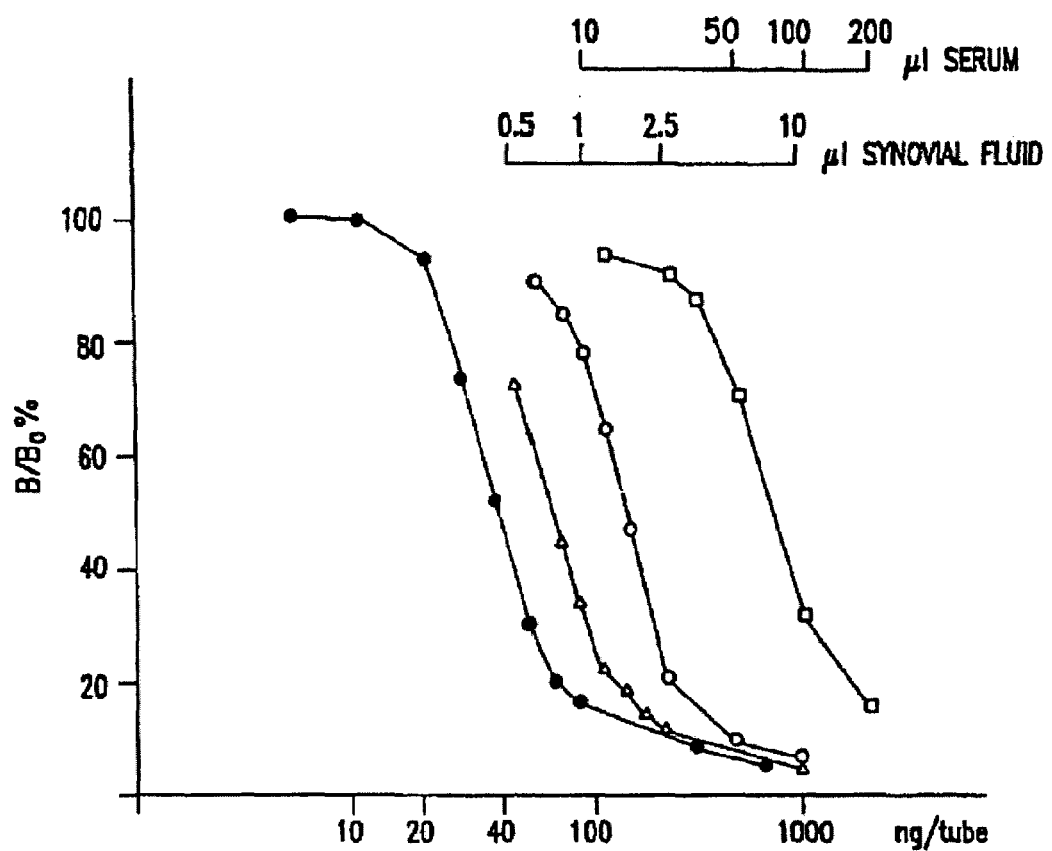
FIG. 2 depicts the results of a radioimmunoassay for YKL-40 in biological samples (serum and synorial fluid) taken from human patients with inflammatory rheumatic joint disease. Purified YKL-40 is indicated by ●. Serum levels of YKL-40 in a healthy person is indicated by ; in serum from a rheumatoid arthritis patient by _, and in synovial fluid of a rheumatoid arthritis patient by □.

The individual serum YKL-40 concentrations in the two patient groups and controls are shown in FIG. 2. The serum YKL-40 concentrations of patients with inflammatory rheumatic disease (median; lower quartile-upper quartile: 138 μg/L; 103-211 μg/l) was not statistically different (p=0.44) from those in patients with osteoarthritis (112 μg/L; 93-152 μg/L). Serum YKL-40 in both patient groups was significantly higher (p<0.001) than that of controls (50 μg/L; 36-64 μg/l). The YKL-40 concentration in knee joint synovial fluid from the patients with inflammatory rheumatic disease (2210 μg/l; 1625-3040 μg/l) was not significantly different from the concentration of the patients with osteoarthritis (1720 μg/l; 1270-1950 μg/l).

Serum levels of YKL-40 can, therefore be related to the incidence of joint disease, particularly inflammatory joint disease. However, distinctions between the different joint diseases evaluated are not apparent from these data

EXAMPLE V

YKL-40 Stability in Serum Assay Samples

To assess the effect of freezing and thawing on YKL-40 antigen in the assay samples, a fresh serum sample was obtained from 6 adults and 10 aliquots of each sample were prepared. One aliquot was kept on ice, and the others were frozen at −20.degree. C. At 60 minute intervals, the aliquots were removed and thawed at room temperature. One sample was kept on ice and the rest refrozen. This procedure was repeated 9 times with no loss of serum YKL-40 reactivity. To assess the effect of long-term storage at room temperature, a fresh serum sample was obtained from 12 adults, and 4 aliquots of each sample were prepared. One aliquot was immediately frozen at −20.degree. C., the others were frozen after 24 hours, 48 hours and 120 hours storage at room temperature, during which time reactivity remained stable.

EXAMPLE VI

Figure 3:
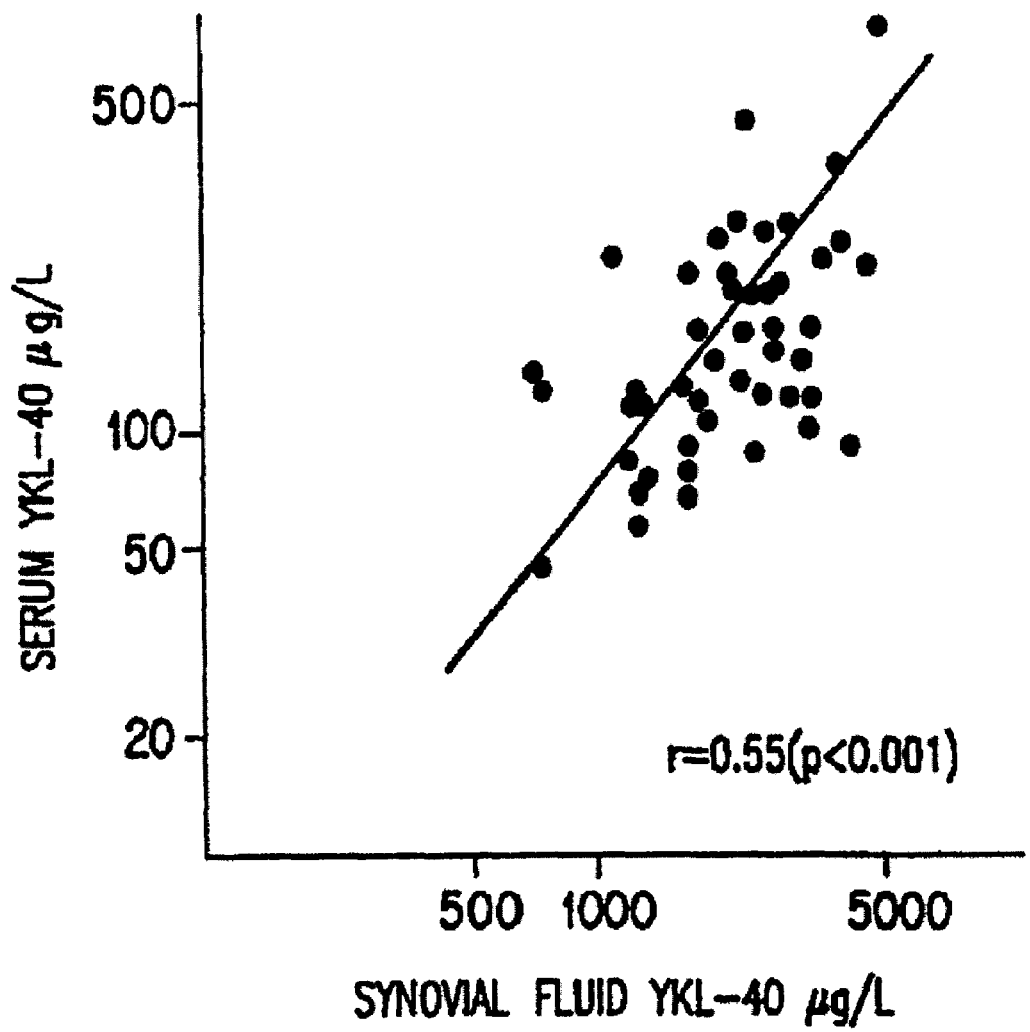
FIG. 3 depicts the results of assays for levels of YKL-40 and other biochemical markers of joint disease in serum taken from human patients diagnosed as having joint disease.

Correlation Between YKL-40 in Serum and Synovial Fluid and Other Biochemical Markers of Inflammation and Cartilage Remodeling As shown in FIG. 3, the YKL-40 concentrations measured in the serum and synovial fluid samples described in Example II were highly correlated and the synovial fluid/serum YKL-40 ratio was high. YKL-40 levels in serum and synovial fluid correlated significantly with serum CRP, synovial fluid IL-6, and synovial fluid M.o slashed. elastolysis levels, which were also measured by assay of these samples as described below. Serum YKL-40 also correlated with serum M.o slashed. elastolysis and serum P-III-NP levels in these samples. The synovial fluid YKL-40 concentrations measured in these samples correlated with a clinical index of knee inflammation. No correlation was found between YKL-40 in serum or synovial fluid and serum IL-6 and synovial fluid P-III-NP levels.

The serum concentration of CRP was determined by nephelometry (Behringwerke, Marburg, Germany). Interleukin-6 (IL-6) activity was determined by bioassay using the highly specific IL-6 dependant mouse hybridoma cell line B13, 29 clone B9 known in the art. The aminoterminal propeptide of type III procollagen (P-III-NP) was measured by a commercially available RIA (P-III-NP RIA kit, Farmos Diagnostica, Oulunsalo, Finland). The elastolytic activity of monocytesimacrophages (M.o slashed.) were investigated with an assay for live M.o slashed. elastolysis described by Jensen, et al. (1991) Scand. J. Rheum. 20:83-90. The results of these assays are shown in Table I, below.

TABLE I

Relationship between serum and synovial fluid concentrations of ykl-40 and other biochemical markers of rheumatoid arthritis

|  | Serum YKL-40 | Synovial Fluid YKL-40 |
| --- | --- | --- |
| Serum CRP | 0.33* | 0.31* |
| Serum IL-6 | 0.26 | −0.10 |
| Synovial fluid IL-6 | 0.60** | 0.47* |
| Serum M. phi. elastolysis | 0.55** | 0.58** |
| Synovial fluid M. phi. elastolysis | 0.64** | 0.58** |
| Serum PIIINP | 0.49 | 0.13 |
| Synovial fluid PIIINP | 0.02 | −0.23 |
| Clinical Knee Index | 0.27 | 0.34* |

*$p < 0.05$;
**$p < 0.01$;
***$p < 0.001$.

EXAMPLE VII

Correlation of Changes in Serum YKL-40 Levels with Progress in the Treatment of Joint Disease This one year, double blind placebo controlled study was primarily conducted in order to evaluate whether (1) YKL-40 relects disease activity in a large group of patients with active rheumatoid arthritis, and, (2) monthly treatment with intravenous methylprednisolone (MP; known to reduce inflammation for 4-8 weeks after intravenous administration) enhanced or accelerated the effect of the disease modifying drugs penicillamine or azathioprine, using YKL-40 as a marker for disease progression and/or amelioration. The study included 97 patients with definite or classic rheumatoid arthritis (RA) as defined by the American Rheumatism Association (see Arnell, et al., Arthritis Rheum., supra).

Blood samples were collected in the morning just before each pulse treatment and plasma YKL-40 was determined by RIA as described in Example IV. The initial median concentration of serum YKL-40 detected in the 97 patients with RA was 174 µg/l (range 40-583 µg/l). Plasma YKL-40 levels in the RA patients were significantly higher (p.gtoreq.0.001) than in 260 healthy adults whose plasma YKL-40 levels were also tested (102 µg/l median of a range of 38-514 µg/l). For comparison, serum hyaluronan and serum C-reactive protein (CRP) levels were also tested in all of the RA patients and in 99 healthy adults (using a radiometric assay for hyaluronan from Pharmacia, Uppsala, Sweden).

Radiography of the hands, wrists and feet of each patient was taken before the start of treatment and again at 360 days. The radiographs were evaluated blind by a radiologist. The presence of erosions at least 1 millimeter deep and any increase or change in the number of erosions after 12 months were noted for clinical significance.

In Table II, the clinical data and initial values of serum YKL-40 and serum hyaluronan in the two treatment groups are shown. The groups were not significantly different.

TABLE II

Clinical Data and Initial Values of Plasma YKL-40 and Serum Hyaluronan in the Two Treatment Groups Methylprednisolone

|  | Methylprednisolone Group N = 31 | Placebo Group N = 26 |
| --- | --- | --- |
| Sex (M/F) ratio | 11/20 | 4/22 |
| Penicillamine/Azathioprine ratio | 20/11 | 18/8 |
| Age Years | 60 (23–79) | 62.5 (32–78) |
| Disease duration years | 9 (1–32) | 7.5 (0–43) |
| ERR mm/hour | 45 (6–118) | 54 (2–110) |

TABLE II-continued

Clinical Data and Initial Values of Plasma YKL-40 and Serum Hyaluronan in the Two Treatment Groups Methylprednisolone

|  | Methylprednisolone Group N = 31 | Placebo Group N = 26 |
|---|---|---|
| Serum CRP mg/L | 23 (1–248) | 42 (1–134) |
| Plasma YKL-40 µg/L | 179 (40–583) | 185 (44–583) |
| Serum Hyaluronan µg/L | 93 (14–1196) | 121 (35–632) |
| # Bone erosions | 15 (0–35) | 11 (0–30) |
| # Swollen joints | 7 (0–19) | 8 (0–30) |
| # Tender joints | 17 (2–45) | 22 (2–41) |

Values are medians (range). The groups were not significantly different in any of the parameters.
ESR = erythrocyte sedimentation rate;
CRP = C-reactive protein;
# = Number.

The patients entered a double blind placebo controlled trial of pulse treatment with 1000 mg intravenously injected methylprednisolone (MP) every 4 weeks for a total of six (6) times, followed by six months without pulse therapy. 7 days after the first pulse therapy the patients were started on penicillamine or azathioprine as described in Hansen, et al. (1990) Br. Med. J., 301: 268. 57 patients completed the trial, taking the same disease modifying drug throughout (31 were treated with MP [penicillamine/azathioprine: 20:11] and 26 with placebo). Eleven patients changed from penicillamine to azathioprine during the study, and 29 were withdrawn from the study owing to adverse reactions or lack of effect during treatment with azathioprine.

Data obtained from the study were analyzed statistically as follows. In order to evaluate the longitudinal changes in serum YKL-40 and serum hyaluronan during treatment, the initial value for each subject was set at 100% and values obtained after institution of treatment were expressed as a percentage of the initial value. The mean differences between groups were evaluated by the Student's t-test for unpaired data. When raw YKL-40 value data was evaluated, comparison between groups were calculated using the non-parametric mann-Whitney test for unpaired differences and the Wilconxon test for paired differences. For these analyses, p values of less than 0.05 were considered significant. Correlations between the different parameters were calculated using the Spearman rho test. For this analysis p values of less than 0.01 were considered to be significant. All analytical tests used are standard in the art.

Figure 4A:
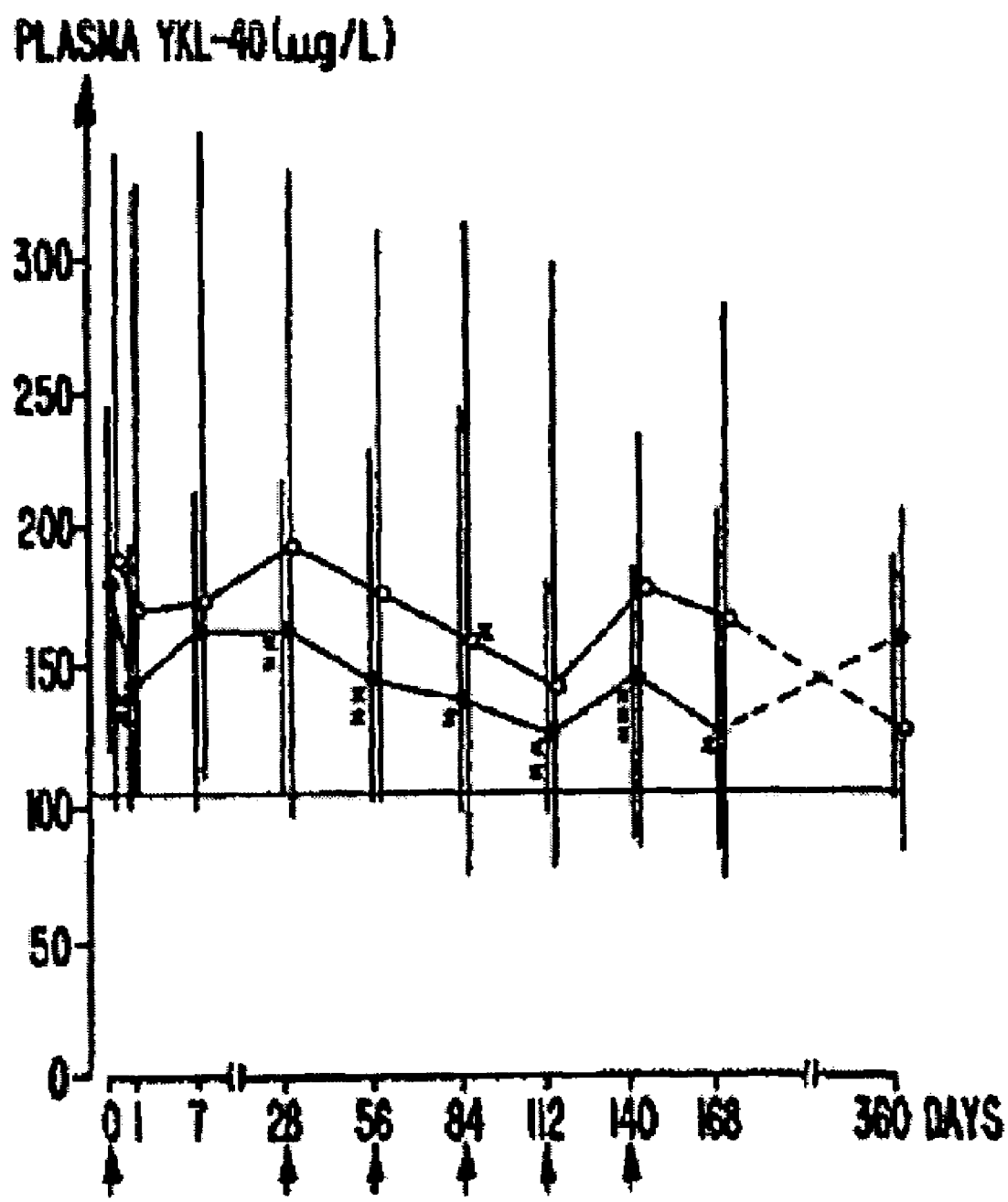
FIGS. 4(a)-(b) depict changes in serum YKL-40 and serum hyaluronan levels in 57 patients with active RA during a one year study period regarding the effects of methylprednisolone (MP) treatment on RA. The patients indicated by ● in the figure received MP treatment, while patients in a control group received a placebo (indicated by ○). All patients received either penicillamine or azathioprine.

FIG. 4(a) illustrates the changes in serum YKL-40 and serum hyaluronan during the one year study period in the 57 patients who completed the trial. YKL-40 levels were significantly lower compared to initial values after MP therapy (o in FIG. 4(a)) was instituted, then returned to initial values after therapy was withdrawn. In contrast, in the group treated only with penicillamine or azathioprine (.smallcircle. in FIG. 4(a)), YKL-40 levels only differed significantly from background after day 84.

The effects of MP treatment on YKL-40 levels were also compared to its effect on other biochemical markers of joint disease. Serum hyaluronan was determined by a radiometric assay using specific hyaluronan-binding protein isolated from bovine cartilage (Pharmacia, Uppsala, Sweden). Serum C reactive protein (CRP) was determined by nephelometry (Beringwerke, Marburg, Germany).

Figure 4B:
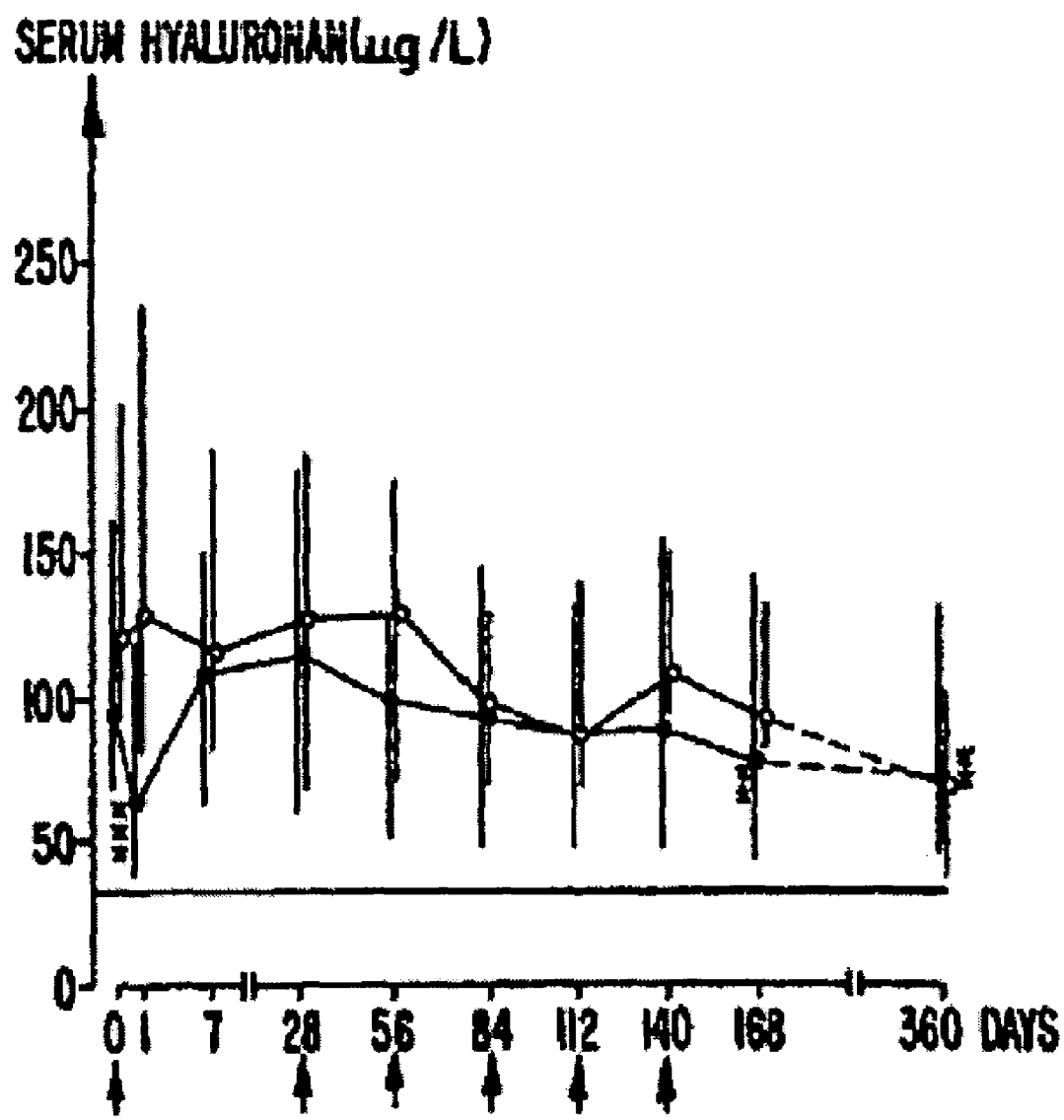

Serum hyaluronan was only significantly decreased in the MP group at day 1 and day 168 (.circle-solid. in FIG. 4(b); the placebo group is indicated by a .smallcircle.), whereas serum CRP was significantly decreased throughout the study period in the MP group and after day 84 in the placebo group (data not shown). The values measured for hyaluronan did not significantly differ between the MP and placebo groups except at day 1 (see, FIG. 4(b)).

Figure 5A:
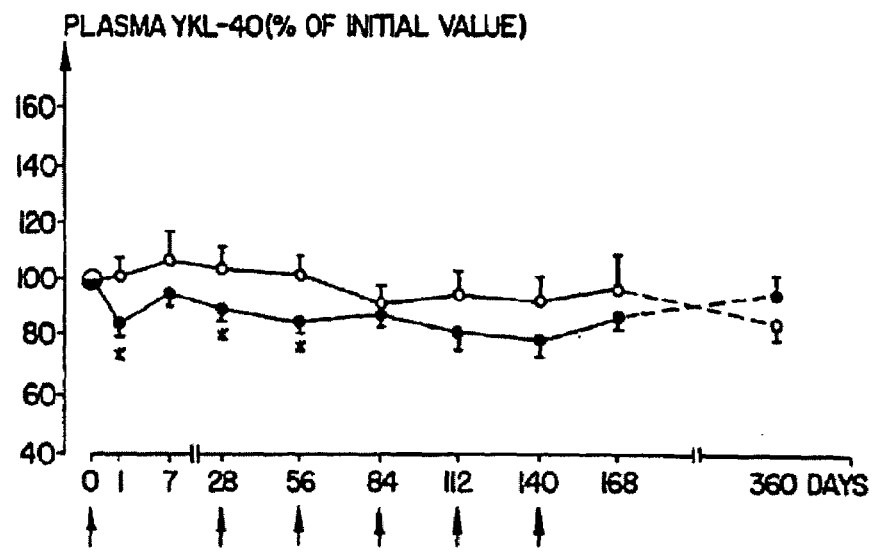
FIGS. 5(a)-(b) depict changes in serum YKL-40 and serum hyaluronan levels in 57 patients with active RA during a one year study period regarding the effects of methylprednisolone (MP) treatment on RA. The patients indicated by ● in the figure received MP treatment, while patients in a control group received a placebo (indicated by ○). All patients received either penicillamine or azathioprine. For each subject, the initial concentration was set at 100%, and all subsequent values were expressed as a percentage of each initial value.
Figure 5B:
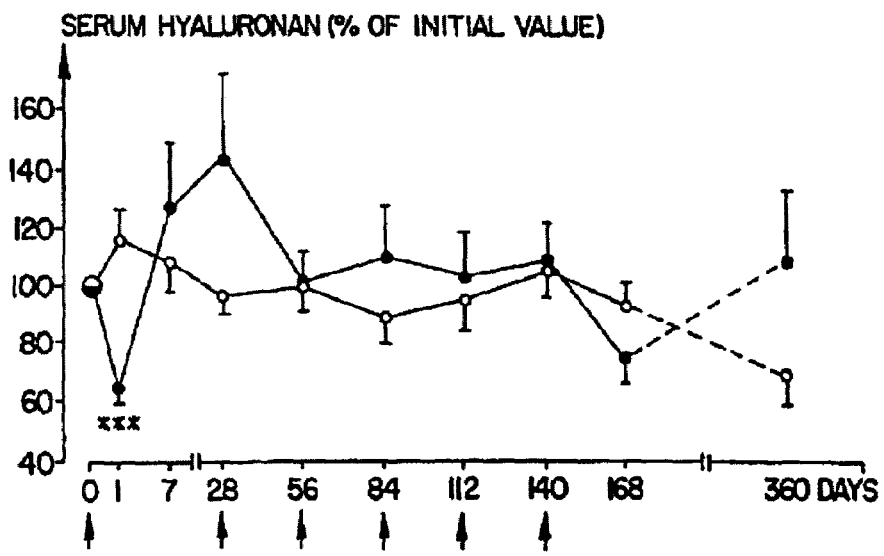

The changes in plasma YKL-40 during the course of the MP treatment was different compared to the changes in serum hyaluronan, as shown in FIGS. 5(a) and (b).

MP therapy therefore produced a significant, albeit transient decrease in plasma YKL-40 which correlated in the first months following treatment to other indicators of a therapeutic response.

EXAMPLE VIII

Relationship of Serum YKL-40 Levels to Survival Rates Following Recurrence of Breast Cancer Serum levels of YKL-40 were measured in a clinical group of 60 breast cancer patients (aged 29-78 years) using the RIA described in Example IV. For comparison, serum YKL-40 levels in a control group of 137 disease-free women (aged 20-79 years) were also measured. These latter measurements define the normal and median YKL-40 values referred to in this example.

The members of the clinical and control groups were, respectively:

1. Clinical Group 60 women aged 29-78 years who had previously been diagnosed with primary breast cancer. They were all potential candidates for systemic antineoplastic treatment. The criteria of entry were: 1) suspicion of distant metastases after primary treatment of localized disease; 2) locally advanced disease or distant metastases at the time of initial diagnosis; and 3) patients with suspected progression of bone metastasis after initial recurrence. Patients who had other primary cancers at any time were not eligible for this study.

39 patients (65%) had received adjuvant therapy. 22 (56%) of these patients had received adjuvant combination chemotherapy with cyclophosphamide, methotrexate and 5-fluorouracil immediately after the removal of the primary tumor. None of the patients had been treated during the previous 12 weeks before the start of the study (i.e., the time of assay sample collection).

2. Control Group

Serum YKL-40 concentrations in 137 healthy women (aged 20-79 years) were established for use as control values. The serum samples were obtained from blood donors who attended the Regional Blood Transfusion Services at Hvidovre Hospital, Denmark, from women working at different museums in Copenhagen, Denmark and from elderly women living in a shared house for elderly in Copenhagen. All these women were healthy (had no known disease), were not taking any medicine and all had a normal liver and kidney function.

The period of time which each patient in the clinical group survived following recurrence of their cancer was observed. The nature of any metastasis of the tumor cells was also characterized in each patient. These data are correlated to the serum YKL-40 levels measured in each patient at the time of recurrence of their cancer.

3. Recurrence

All serum analyses reported here were determined on blood samples obtained from each of 60 women at the time of their entrance into the study. Forty-seven of these women entered the study at the time that breast cancer recurrence was first suspected (criteria 1). Further tests revealed that 6 of these women did not in fact have breast cancer recurrence. Six women entered the study because they had locally advanced disease or distant metastases at the time of initial breast cancer diagnosis (criteria 2) and 7 women entered the study because they were suspected to have bone metastases 9 to 27 months after their first recurrence of breast cancer (criteria 3).

4. Survival After Recurrence.

Figure 8:
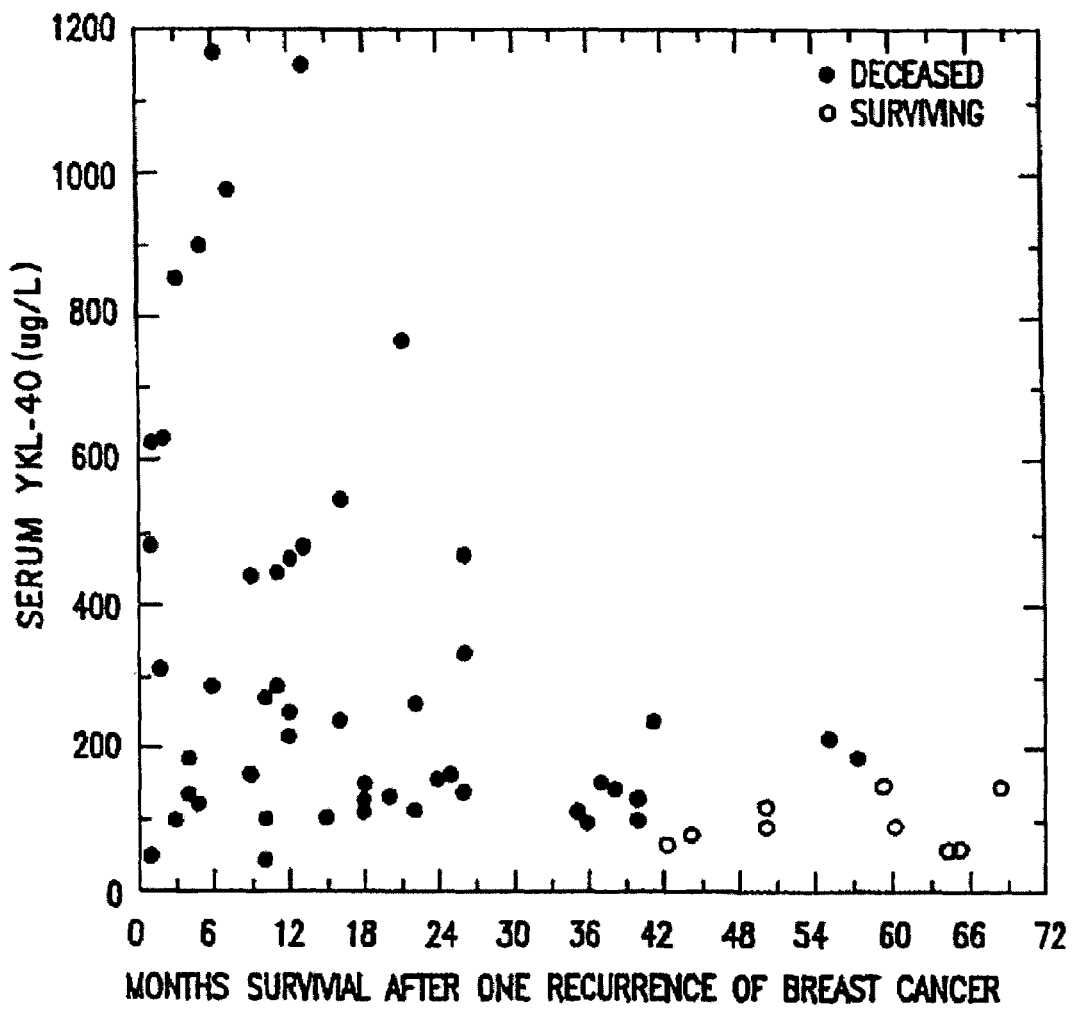
FIG. 8 is a graph which identifies the serum levels of YKL-40 in breast cancer patients (measured as described with respect to FIG. 6) and shows if and when each patient subsequently died as a result of their illness. The data are identified according to the selection criteria for entrance into the study (described in Example VII) that were met by the patient. .circle-solid. or .circle-solid.=patients meeting selection criteria #1; □ or ■=patients with no recurrence of breast cancer; X=patients meeting selection criteria #2; and, or .Δ=patients meeting selection criteria #3. Open and X symbols denote patients still alive at the point in time noted; closed symbols denote patients who had died by the time noted.

At the time of analysis 9 of the 60 patients were still alive. The median survival after recurrence in the 41 patients with first recurrence of breast cancer was 16 months (25-75% fractiles: 9-26 months) and in all 60 patients the corresponding values were 16 months (7-40) months). Table III summarizes the univariate survival data for 17 variables. Age, degree of anaplasia, serum LDH, serum AP, serum albumin and serum YKL-40 were all significant univariate prognostic factors in the 60 patients. FIG. 8 shows the individual serum YKL-40 concentration in relation to months of survival after recurrence. At the time of follow-up all 25 patients with high serum YKL-40 were dead compared to 26 of 35 patients with normal serum YKL-40. Sixty-seven percent (20/30) of the patients who died within 16 months had elevated serum YKL-40.

Figure 6:
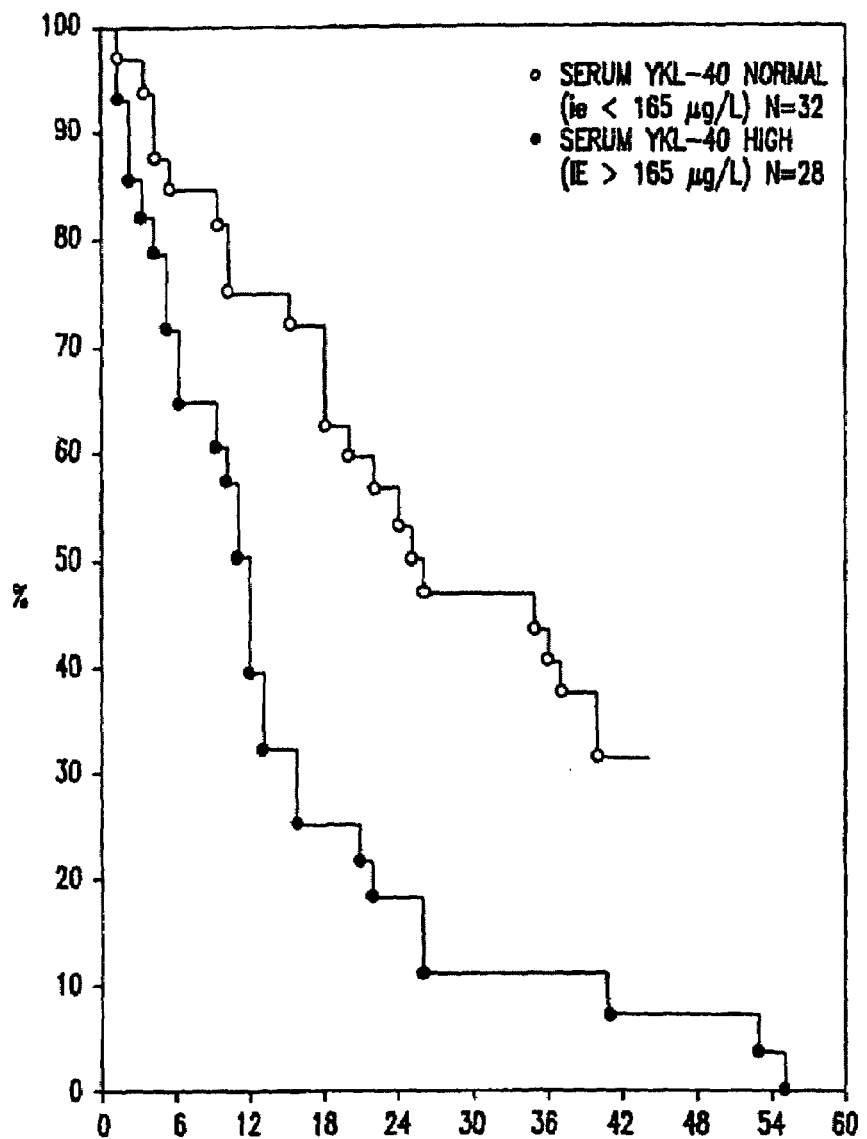
FIG. 6 shows a Kaplan-Meier survival curve, which relates the serum levels of YKL-40 measured in 60 breast cancer patients (aged 29-78 years) following recurrence and metastasis of their cancers to the length of time that each patient subsequently survived.

The Kaplan-Meier survival curves according to serum YKL-40 levels in the 41 patients with first recurrence of breast cancer are presented in FIG. 6. Although the number is small, the survival of the two groups (patients with normal or high serum YKL-40) is explicitly different. In the 41 patients with first recurrence of breast cancer the survival rates after 18 months were 60% for patients with normal and 24% for patients with high serum YKL-40 ($p<0.0009$) If the calculations were performed on all 60 patients the survival rates after 18 months were 63% and 20% for patients with normal and high levels of serum YKL-40 ($p<0.0001$).

As shown in FIG. 6, 76% of the clinical group members still alive after 16 months following recurrence had serum YKL-40 levels of 164 µg/L or less. 85% of the members who lived longer than 30 months following recurrence had serum YKL-40 levels of 164 µg/L or less. Thus, patient survival after the first recurrence of the cancer was significantly prolonged ($p=0.0009$) in the group of patients with normal serum YKL-40 compared to the patients with serum YKL-40 levels equal to or greater than about 164 µg/l, and particularly in those patients with serum YKL-40 levels equal to or greater than about 207 µg/l ("prognostically significant levels" of YKL-40). These data indicate that an elevated serum YKL-40 level correlates to decreased survival of patients with advanced breast cancer, thus suggesting that where such levels are detected, more aggressive treatment protocols may be warranted. Serum YKL-40 measurements will be especially informative where, as was the case among the patients in this study, the clinical symptoms of patients who died more quickly did not differ substantially from the clinical symptoms of patients who survived for longer periods following recurrence of their cancers.

Similar Kaplain-Meier curves based on serum levels of other blood proteins (such as serum alkaline phosphatase) measured at the same time as the YKL-40 levels did not correlate as clearly to survival rate among the clinical group members.

5. Location of Metastases.

Among the 60 women in the study, thirty patients (50%) had soft tissue recurrence; bone metastases (as detected by X-ray or bone biopsy) were found in 40 patients (67%); and visceral metastases (lung, pleura or liver) occurred in 19 (32%) patients.

Figure 9:
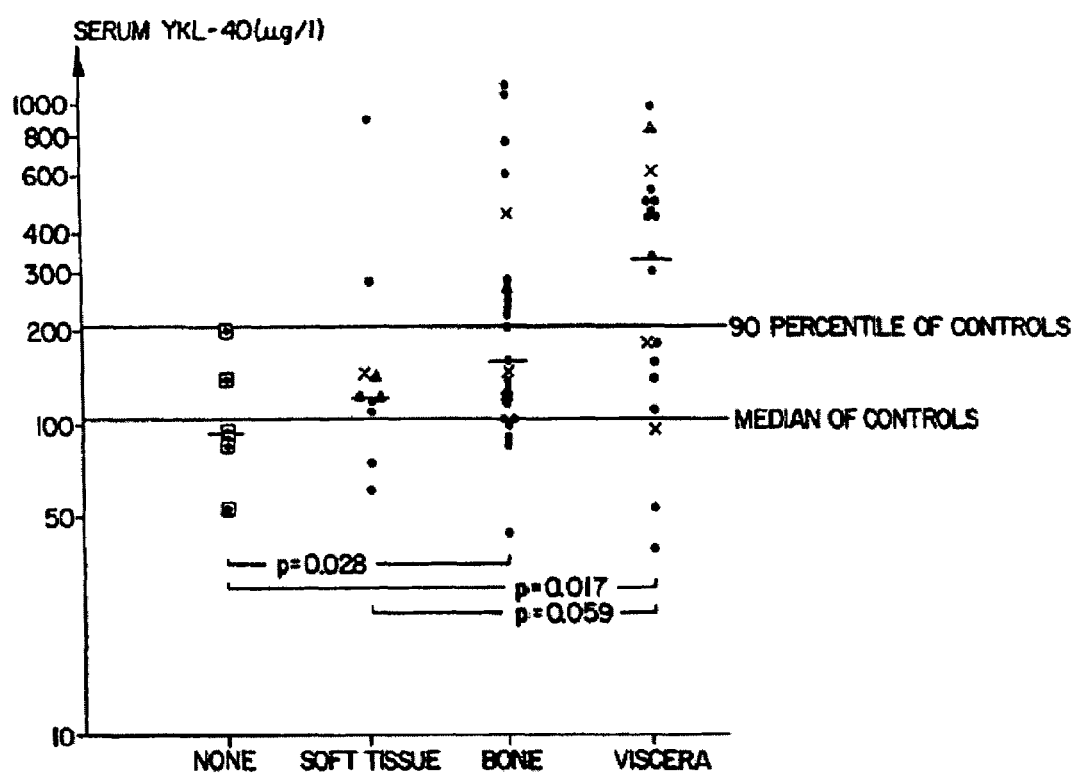
FIG. 9 depicts YKL-40 levels detected in the sera of patients in a study regarding recurring, metastatic breast cancer in relation to the principal site of metastasis (if any) of the cancer. The data are identified according to the selection criteria for entrance into the study (described in Example VIII) that were met by the patient.=patients meeting selection criteria #1; □=patients with no recurrence of breast cancer; X=patients meeting selection criteria #2; and,=patients meeting selection criteria #3.

FIG. 9 shows the distribution of serum YKL-40 according to main sites of metastases among the patients in the clinical group. All six patients without metastases had a normal serum YKL-40 level. The Kruskal-Wallis test of the YKL-40 levels between the groups was highly significant ($p=0.03$). The median serum YKL-40 in patients with visceral or bone metastases was significantly higher ($p<05$) compared to the levels in patients without metastases and to the level in healthy age-matched women (102 µg/l, $p<0.001$). If only the 41 patients with first recurrence of breast cancer were used in the calculations similar significance of difference were found.

Twenty-five of the 54 patients with metastases had serum YKL-40 levels above the cut-off level of 207 µg/l. In patients with soft tissue recurrence (n=10), the median serum YKL-40 was 123 µg/L, and only 2 patients had elevated serum YKL-40. One of these 2 patients had a very high serum YKL-40 concentration (904 µg/l) and died after 5 months. At the time of blood sampling, this patient had pleuraeffusion but microscopy did not reveal malignant cells. In patients with bone metastases (=/-soft tissue recurrence (N=25)) the median serum YKL-40 was 157 µg/l and 12 of these patients (48%) had elevated serum YKL-40. Four patents had only visceral metastases and serum YKL-40 was above normal in 3 of these patients (75%).

FIG. 12 illustrates the individual serum YKL-40 concentrations in relation to the presence of bone metastases on X-ray examination. Since serum YKL-40 levels are increased in patients with viscera metastases we only evaluated the diagnostic value in patients without visceral involvement (N=41). Serum YKL-40 was significantly elevated ($p<0.05$) in patients with .gtoreq.2 bone metastases compared to patients with only one or no bone metastasis. Four patients with a normal X-ray had elevated serum YKL-40. However, two of these patients had a positive bone scanning and biopsies revealed bone marrow carcinosis, and other two developed radiographic bone metastases within 6 months.

Figure 10:
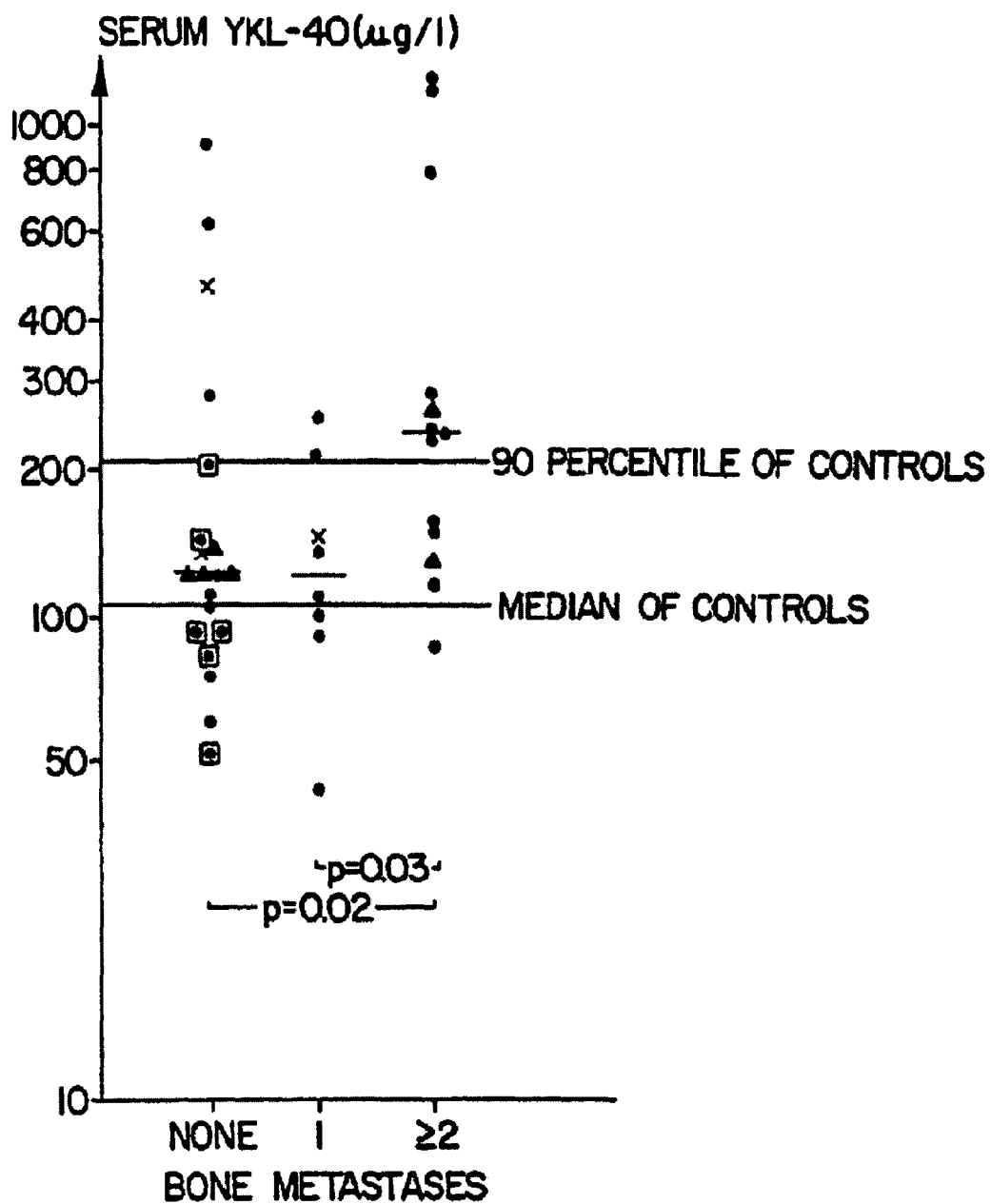
FIG. 10 depicts YKL-40 levels detected in the sera of patients in a study regarding recurring breast cancer with metastasis to bone but without visceral involvement of the cancer. The data are identified according to the selection criteria for entrance into the study (described in Example VIII) that were met by the patient. .circle-solid.=patients meeting selection criteria #1; □=patients with no recurrence of breast cancer; X=patients meeting selection criteria #2; and,=patients meeting selection criteria #3.

Relating serum YKL-40 levels to the presence or absence of one or more bone metastases, YKL-40 levels were elevated in clinical group members with positive test results as opposed to negative test results. In addition, YKL-40 levels were elevated in positive test result members with more than one metastasis to bone as opposed to members with one metastasis to bone (see, FIG. 10).

Figure 7:
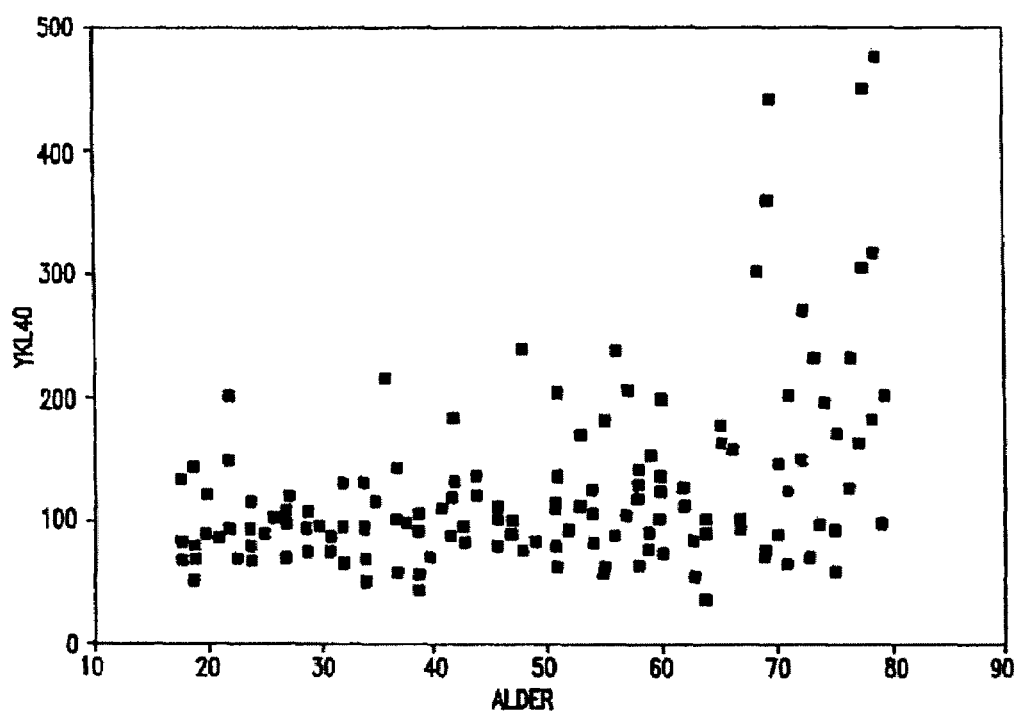
FIG. 7 depicts levels of YKL-40 detected in the sera and synovial fluid from 137 disease-free women, aged 2079 years.

There was no clear relationship between the level of serum YKL-40 and other clinical parameters, such as the menopausal status of each patient (see Tables III and IV, below). However, serum YKL-40 values were elevated compared to normal levels in 75% of the patients with visceral metastasis and 48% of patients with metastases to bone. There also did not appear to be any clear relationship between YKL-40 levels and age, although, as shown in FIG. 7, aberrant levels of YKL-40 did not appear in healthy (control group) women below age 70. Thus, particularly as compared to other blood proteins measured (see Tables III-IV), YKL-40 levels have diagnostic value with respect to metastases of breast cancer cancer cells to bone and viscera.

6. Cox Regression Analysis

The initial Cox model included univariate significant blood tests and duration of recurrence free interval. Serum albumin was not included because the value was only registered in 40% of the patients. The initial model showed that only serum YKL-40 and serum LDH were independent prognostic factors on survival after recurrence in the 60 patients (Table III). Backward and forward elimination procedures eliminated all covariates except serum YKL-40 (p=0.001) and serum LDH (p=0.01). If only the 41 patients with first recurrence of breast cancer were included in the calculations backward and forward elimination procedures again eliminated all covariates except serum YKL-40 (p=0.0004 and serum LDH (p=0.037).

Based on the estimated survival pattern for the 4 combinations of the two serum YKL-40 levels and the two levels of serum LDH, the calculated survival rate after 12 months for patients with normal serum LDH and normal and elevated serum YKL-40 was 83% and 56%, respectively. Among patients with increase serum LDH levels the 12 months survival rate was 67% for patients with normal and 28% for patients with high serum YKL-40.

TABLE III

Serum YKL-40 in relation to different clinical parameters in 60 women with first recurrence of breast cancer (cox univariate survival analysis).

| Variable | Categories | # of patients # alive | Median Survival Months (25%–75%) | P (log rank) |
|---|---|---|---|---|
| Age | ≦50 | 30 (8) | 18 (10–55+) | 0.04 |
| Years | >50 | 30 (1) | 16 (6–26) | |
| Menopausal | pre- | 30 (7) | 18 (10–55+) | 0.07 |
| Status | post- | 29 (2) | 16 (6–26) | |
| Size of primary | ≦2 | 25 (5) | 22 (10–37) | 0.46 |
| tumor (cm) | 3–4 | 16 (1) | 16 (10–37) | |
| | >4 | 18 (2) | 12 (5–21) | |
| Axillary node | negative | 18 (5) | 22 (10–41+) | 0.29 |
| status | positive | 34 (3) | 18 (10–41) | |
| Degree of | low | 13 (1) | 12 (4–18) | 0.01 |
| anaplasia | high | 15 (3) | 26 (11–56) | |
| Estrogen receptor | negative | 10 (2) | 10 (6–18+) | 0.99 |
| status | positive | 18 (2) | 21 (11–37) | |
| Recurrence Free | ≦24 | 32 (4) | 13 (5–26) | 0.18 |
| interval (months) | >24 | 28 (5) | 21 (10–41) | |
| Dominant site of | soft tissue | 10 (4) | 18 (6–50) | 0.24 |
| metastasis | bone | 25 (1) | 18 (12–26) | |
| | viscera | 19 (1) | 9 (3–16) | |
| Blood | | | | |
| Haemoglobin | ≦7.0 | 11 (8) | 9 (2–16) | 0.24 |
| mmol/l | >7.0 | 49 (1) | 20 (10–41) | |
| Serum ASAT | ≦30 | 38 (7) | 20 (10–47) | 0.38 |
| U/l | >30 | 20 (2) | 12 (4–26) | |
| Serum LDH | ≦400 | 29 (8) | 25 (15–53+) | 0.00 |
| U/l | >400 | 31 (1) | 10 (5–21) | |
| Serum AP | ≦275 | 40 (9) | 22 (11–56) | 0.00 |
| U/l | >275 | 20 (0) | 10 (3–18) | |
| Serum Albumin | ≦600 | 8 (0) | 7 (3–11) | 0.00 |
| mg/l | >600 | 16 (1) | 23 (18–41) | |
| Serum | ≦100 | 16 (2) | 9 (2–16) | 0.13 |
| Prothrombin % | >100 | 33 (4) | 20 (10–35) | |
| Serum Ca++ | ≦1.35 | 13 (1) | 12 (7–35) | 0.24 |
| mmol/l | >1.35 | 5 (0) | 12 (2–18) | |
| Serum BGP | ≦2 | 23 (5) | 13 (4–56) | 0.67 |
| mmol/l | 2–2.9 | 19 (1) | 18 (7–37) | |
| | >2.9 | 18 (3) | 24 (12–47) | |
| Serum YKL-40 | ≦207 | 35 (9) | 24 (15–53+) | 0.00 |
| µg/ml | >207 | 25 (0) | 11 (6–21) | |
| All | | 60 (9) | 16 (7–40) | |

TABLE IV

Cox model for survival for patients entering staging of recurring breast cancer.

| Covariate | Categories | Coefficient β | S.E. | P (Wald's Test) |
|---|---|---|---|---|
| Initial Model | | | | |
| Serum YKL-40 (µg/l) | ≦207, >207 | 1.04 | 0.36 | 0.00 |
| Serum BGP (mmol/l) | ≦2, 2–2.9, >2.9 | −0.20 | 0.19 | 0.31 |
| Serum ASAT (U/l) | ≦30, >30 | −0.25 | 0.33 | 0.44 |
| Serum LDH (U/l) | ≦400, >400 | 0.66 | 0.37 | 0.08 |
| Serum AP (U/l) | ≦275, >275 | 0.46 | 0.40 | 0.26 |
| Haemoglobin (mmol/l) | ≦7, >7 | −0.03 | 0.42 | 0.94 |
| Recurrence free interval (months) | ≦24, >24 | 0.25 | 0.31 | 0.41 |
| Final Model* | | | | |
| SerumYKL-40 (µg/l) | ≦207, >207 | 1.11 | 0.33 | 0.00 |
| Serum LDH (U/l) | ≦400, >400 | 0.78 | 0.31 | 0.01 |

*After backwared elimination (p value to remove: 0.01; p value to enter: 0.15).

EXAMPLE IX

Detection and Quantification of YKL-40 in Serum and Synovia of Osteoarthritis Patients and Comparison to Levels Detected in Patients with Knee Trauma Accelerated metabolism of connective joint tissue is known to occur in degenerative joint disease (such as osteoarthritis), as well as in inflammatory joint diseases (such as RA). However, beyond that similarity, the pathogenesis of degenerative and inflammatory joint disease are dissimilar. For example, degenerative joint disease is believed to be associated with microfractures in bone caused by repeated exposure to weight and impact loading. In healing, the fractures become covered with stiff and thickened subchondral bone that poorly absorbs the energy associated with weight loading. The chondrocytes in articular cartilage are therefore subjected to pressure deflected from the bone, stimulating chondrocyte growth and metabolism. Initially, the body is able to make repairs as necessary, but eventually the degenerative process predominates, resulting in loss of cartilage (see, e.g., Harrison's Principles of Internal Medicine, 11th ed., McGraw-Hill, 1987, at page 1456. et seq.).

In contrast, the loss of cartilage in inflammatory joint disease is believed to be caused by inflammation of the synovia. Over time, the synovia forms villi that will project into the joint cavity. Disposition to RA in particular is believed to be conferred genetically, with an as yet unelucidated association with HLA-DR4, a class II major histocompatibility complex molecule. Inflammatory joint disease produces fairly specific clinical manifestations, including morning stiffness, a symptom that distinguishes inflammatory from non-inflammatory joint disease (see, e.g., Harrison's Principles of Internal Medicine, supra at page 1423, et seq.).

Given the differences in pathogenesis and pathology between inflammatory and non-inflammatory joint disease, it would not be predictable that a marker for one would serve as a marker for the other. It was therefore surprising to discover that YKL-40 levels are elevated to a diagnostically significant degree not only in body fluids of RA patients, but also in body fluids of osteoarthritis patients.

This discovery was made in a study comparing sera and synovia YKL-40 levels from patients with traumatic knee injuries and osteoarthritis (late stage) to serum YKL-40 levels from healthy children and adults, the latter of which data confirmed baseline "normal" levels of serum YKL-40.

1. Control Group 476 normal children (aged 6-17 years; 236 girls and 240 boys) participated in the study. 275 adults (aged 18-79 years; 146 women and 129 men) also participated in the study. Each participant was examined and determined to be healthy according to conventional medical standards.

2. Patient Group 96 adults (aged 18-79 years; 37 women and 59 men) participated in the study. Clinically, these participants were grouped as follows: Group A=12 patients who had knee pain leading to arthroscopy, but who were determined to be free of knee pathology; Group B=18 patients without synovitis, but with an abnormal arthroscopy indicating trauma; Group C=22 patients with mild to moderate synovitis; Group D=18 patients with acute severe synovitis; Group E=10 patients with chronic post-traumatic synovitis; Group F=16 patients with osteoarthritis (late stage, knee). Serum was collected from each patient; synovia was only available in sufficient quantity for analysis from 51 patients.

The patients were determined to be otherwise healthy according to conventional medical standards. None of the patients were taking medication except 14 of the osteoarthritis patients, who were taking non-steroidal anti-inflammatory drugs.

Serum and synovial fluid YKL-40 levels were determined as described in Example IV. Statistical analyses of assay results were performed using a commercially available software program to perform analyses according to standard methods (SSPS software). Comparisons between groups were calculated using the non-parametric Mann-Whitney and Kruskal-Wallis tests known in the art. Correlations between the different parameters were calculated using the Spearman rho test known in the art; p values of less than 0.05 were considered to be significant.

The data obtained from this study are set forth below.

TABLE V

Serum YKL-40 concentrations (μg/l) in healthy subjects.

| Age Group Years | N | Female Median (10–90% tile) μg/l | N | Male Median (10–90% tile) μg/l |
|---|---|---|---|---|
| 7–9 | 54 | 76 (60–113) | 58 | 77 (57–105) |
| 10–12 | 70 | 78 (61–107) | 87 | 79 (62–103) |
| 13–15 | 78 | 82 (62–125) | 70 | 83 (62–114) |
| 16–17 | 34 | 90 (67–122) | 25 | 86 (72–122) |
| All | 236 | 79 (62–114) | 240 | 80 (61–107) |
| 18–19 | 9 | 75 | 7 | 94 |
| 20–29 | 20 | 95 (71–122) | 21 | 92 (75–137) |
| 30–39 | 20 | 95 (54–141) | 20 | 101 (75–154) |
| 40–49 | 21 | 100 (77–174) | 17 | 124 (76–212) |
| 50–59 | 29 | 111 (64–204) | 25 | 125 (77–219) |
| 60–69 | 21 | 101 (59–351) | 24 | 111 (66–246) |
| 70–79 | 24 | 168 (69–385) | — | — |

TABLE V-continued

Serum YKL-40 concentrations (μg/l) in healthy subjects.

| Age Group Years | N | Female Median (10–90% tile) μg/l | N | Male Median (10–90% tile) μg/l |
|---|---|---|---|---|
| All | 144 | 101 (69–205) | 116 | 103 (75–213 |

TABLE VI

Characteristics of the patients.

| Clinical Diagnosis | # Serum | Age Years | Serum YKL-40 (μg/l) | SF YKL-40 (μg/l) |
|---|---|---|---|---|
| Normal Knee[§] | 12/0 | 27 (18–55) | 86*** (72–292) | — |
| Torn anterior cruciate ligaments | 7/4 | 28 (26–34) | 89** (66–117) | 712* (336–1358) |
| Torn medial or lateral menisci | 18/12 | 34 (22–49) | 118** (72–233) | 1407 (312–9560) |
| Early stage knee osteo-arthritis | 17/10 | 50 (27–73) | 112** (29–315) | 1306 (500–7296) |
| Late stage knee osteo-arthritis | 16/15 | 71 (61–79) | 195 (88–1648) | 1944 (279–5216) |
| Chondro-malacia | 5/1 | 34 (19–45) | 85** (60–187) | 912 |
| Osteo-chondrocyte | 4/1 | 38 (26–54) | 100* (76–158) | 3540 |
| Acute severe synovitis | 3/1 | 28 (23–31) | 232 (107–287) | 1928 |
| Others[§§] | 14/7 | 23 (18–76) | 83 (63–226) | 878* (201–2140) |

SF = Synovial fluid.
Values are median (range).
*p < 0.05
**p < 0.01
***p < 0.001 vs. the level in patients with late stage knee osteoarthritis.
[§]Patients who had knee pain leading to arthroscopy, but in whom arthroscopy, radiologic studies of the knee, and blood chemistry studies failed to reveal any pathologic condition related to the knee pain.
[§§]Patients with minor arthroscopic changes of the knee joint. They had one of the following diagnoses: 1) Light or acute posttraumatic synovitis (N = 8); 2) Slight defect of one of the menisci (N = 1); 3) Plicae synovitis (N = 3); 4) Mus articuli genus (N = 1); or 5) Patella alignment (N = 1).

In summary, patients with late stage knee osteoarthritis had significantly higher (1.5 to 2 times greater) levels of YKL-40 in sera and synovia as compared to other participants in the patient group and control group (see, Tables V and VI). Approximately 10 times greater levels of YKL-40 were found in synovia as compared to sera, presumably reflecting local production of YKL-40. Because cartilage is present in relatively low amounts in the osteoarthritic knee, it may be assumed that a significant proportion of the YKL-40 found in synovia is synthesized in the synovium, either through synovial cell hyperplasia or increased secretion of YKL-40 by synovial cells. This hypothesis is further supported by the observation that YKL-40 levels were significantly higher (elevated 7 to 16 fold) in patients with severe synovitis as compared to patients with mild or no synovitis. However, it is also possible that YKL-40 is secreted into synovial fluid by chondrocytes. Whatever its source, it appears likely that, in contrast to cases of knee trauma, YKL-40 acts on matrix constituents to degrade them after onset of osteoarthritis or other connective tissue disease associated with YKL-40.

EXAMPLE X

Detection of Serum YKL-40 Levels in Sera from Patients with Alcoholic Cirrhosis and from Adults with Healthy Liver Tissue 39 adults participated in this study: 16 patients with normal liver function (7 women and 9 men; aged 35-74 years) and 23 patients with liver disease (8 women and 15 men; aged 31-75 years). Of the adults with normal liver function, 7 were healthy, 7 had been diagnosed with hypertensive arterialis, 1 had been diagnosed with hypertensive renovascularis, and 1 with ischaemia intestinalis. Of the adults with abnormal liver function, 18 had alcoholic cirrhosis with active hepatitis, 2 had alcoholic cirrhosis without active hepatitis, 2 had hepatitis of unknown origin, and 1 had steatosis hepatitis. At the time of the study, none of the patients were consuming alcohol.

After an overnight fast, the patients were catheterized under local anesthesia in the hepatic vein (from 20 patients with liver disease and 14 with normal liver function) or the renal vein (17 patients with liver disease and 13 patients with normal liver function). Blood samples were obtained from the femoral artery and the organ vein in each patient then analyzed by radioimmunoassay as described in Example IV.

Using the data from the healthy adults reported in Example IX for a control reference, comparisons were made with the data collected from the above-described patients. The statistical analyses were performed as described in Example IX. The arteriovenous extraction ratio was determined as: $E = C_a - C_v / C_a$, where $C_a$ is the YKL-40 immunoreactivity in femoral arterial plasma and $C_v$ is the YKL-40 immunoreactivity in plasma from the renal vein. The renal extraction ratios of the cirrhotic patients and controls were not significantly different; i.e., 0.051 (range=0.0076 to 0.14) and 0.028 (range=−0.0294 to 0.3040), respectively. However, the patients with liver disease had very high YKL-40 levels compared to the levels detected in samples from patients with normal liver function ($p < 0.001$).

Median YKL-40 serum values detected in arterial and venous blood from patients with liver disease are compared to median values detected in arterial and venous blood from patients with normal liver function. As shown in Table VI, the former values were approximately 4 times greater than the latter values (p less than 0.001), strongly indicating that YKL-40 is associated with degeneration of liver tissue.

TABLE VIII

Plasma YKL-40 concentrations (μg/l) in patients with liver disease compared to patients with normal liver function.

| | Liver Disease | Controls | Significance of difference |
|---|---|---|---|
| Artery | 495 (101–2360) N = 20 | 106 (60–248) N = 14 | p < 0.001 |
| Hepatic Vein | 499*** (106–2568) N = 20 | 111** (64–257) N = 14 | p < 0.001 |
| Artery | 493 (100–2920) N = 17 | 125 (53–250) N = 13 | p < 0.001 |
| Renal Vein | 424*** (96–2760) N = 17 | 108* (48–243) N = 13 | p < 0.001 |

*p < 0.05
**p < 0.01
***p < 0.001

The invention being fully described, it will be apparent to those of skill in the art that modifications may be made to the embodiments described above without departing from the spirit or scope of the invention.

---

SEQUENCE LISTING

```
<160> NUMBER OF SEQ ID NOS: 4

<210> SEQ ID NO 1
<211> LENGTH: 25
<212> TYPE: PRT
<213> ORGANISM: Homo sapiens
<220> FEATURE:
<221> NAME/KEY: misc_feature
<222> LOCATION: (20)..(20)
<223> OTHER INFORMATION: Xaa  is unidentified amino acid

<400> SEQUENCE: 1

Tyr Lys Leu Val Cys Tyr Tyr Thr Ser Trp Ser Gln Tyr Arg Glu Gly
1               5                   10                  15

Asp Gly Ser Xaa Phe Pro Asp Ala Leu
            20                  25

<210> SEQ ID NO 2
<211> LENGTH: 19
<212> TYPE: PRT
<213> ORGANISM: Homo sapiens

<400> SEQUENCE: 2

Leu Asn Thr Leu Lys Asn Arg Asn Pro Asn Leu Lys Thr Leu Leu Ser
1               5                   10                  15

Val Gly Gly
```

<210> SEQ ID NO 3
<211> LENGTH: 7
<212> TYPE: PRT
<213> ORGANISM: Homo sapiens

<400> SEQUENCE: 3

Leu Arg Leu Gly Ala Pro Ala
1               5

<210> SEQ ID NO 4
<211> LENGTH: 1681
<212> TYPE: DNA
<213> ORGANISM: Homo sapiens

<400> SEQUENCE: 4

| | | | | | |
|---|---|---|---|---|---|
| ctaggtagct | ggcaccagga | gccgtgggca | agggaagagg | ccacaccctg | ccctgctctg | 60 |
| ctgcagccag | aatgggtgtg | aaggcgtctc | aaacaggctt | tgtggtcctg | gtgctgctcc | 120 |
| agtgctgctc | tgcatacaaa | ctggtctgct | actacaccag | ctggtcccag | taccgggaag | 180 |
| gcgatgggag | ctgcttccca | gatgcccttg | accgcttcct | gtgtacccac | atcatctaca | 240 |
| gctttgccaa | tataagcaac | gatcacatcg | acacctggga | gtggaatgat | gtgacgctct | 300 |
| acggcatgct | caacacactc | aacaacacga | accccaacct | gaagactctc | ttgtctgtcg | 360 |
| gaggatggaa | ctttgggtct | caaagatttt | ccaagatagc | ctccaacacc | cagagtcgcc | 420 |
| ggactttcat | caagtcagta | ccgccatttc | tgcgcaccca | tggctttgat | gggcgtgacc | 480 |
| ttgcctggct | ctaccctgga | cggagagaca | acaccatttt | accacccta | atcaaggaaa | 540 |
| tgaaggccga | atttataaag | gaagcccagc | agggaaaaa | gcagctcctg | ctcagcgcag | 600 |
| cactgtctgc | ggggaaggtc | accattgaca | gcagctatga | cattgccaag | atatcccaac | 660 |
| acctggattt | cattagcatc | atgacctacg | attttcatgg | cgcctggcgt | gggaccacag | 720 |
| gccatcacag | tcccctcagg | cgaggtcagg | aggatgcaag | tcctgacaga | ttcagcaaca | 780 |
| ctgactatgc | tgtggggtac | atgttgaggc | tgggggctcc | tgccagtaag | ctggtgatgg | 840 |
| gcatccccac | cttcgggagg | agcttcactc | tggcttcttc | tgagactggt | gttccagcgc | 900 |
| caatctcagg | accgggaatt | ccaggccggt | tcaccaagga | ggcagggacc | cttgcctact | 960 |
| atgagatctg | tgacttcctc | cgcggagcca | cagtccatag | aaccctcggc | cagcaggtcc | 1020 |
| cctatgccac | caagggcaac | cagtgggtag | gatacgacga | ccaggaaagc | gtcaaaagca | 1080 |
| aggtgcagta | cctgaaggat | aggcagctgg | caggcgccat | ggtatgggcc | ctggacctgg | 1140 |
| atgacttcca | gggctccttc | tgcggccagg | atctgcgctt | ccctctcacc | aatgccatca | 1200 |
| aggatgcact | cgctgcaacg | tagccctctg | ttctgcacac | agcacggggg | ccaaggatgc | 1260 |
| cccgtccccg | tctggctggc | cgggagcctg | atcacctgcc | ctgctgagtc | ccaggctgag | 1320 |
| cctcagtctc | cctcccttgg | ggcctatgca | gaggtccaca | cacacagat | ttgagctcag | 1380 |
| ccctggtggg | cagagaggta | cacacttgtt | gatgattaat | ggaaatgttt | acagatcccc | 1440 |
| aagcctggca | agggaatttc | ttcaactccc | tgcccctag | ccctccttat | caaggacac | 1500 |
| cattttggca | agctctatca | ccaaggagcc | aaacatccta | caagacacag | tgaccatact | 1560 |
| aattataccc | cctgcaaagc | cagcttgaaa | ccttcactta | ggaacgtaat | cgtgtcccct | 1620 |
| atcctacttc | cccttcctaa | ttccacagct | gctcaataaa | gtacaagagt | ttaacagtgt | 1680 |
| g | | | | | | 1681 |

What is claimed is:

1. An isolated antibody that specifically binds YKL-40.

2. The antibody of claim 1, wherein said antibody is a monoclonal antibody.

3. The antibody of claim 1, wherein said antibody is a polyclonal antibody

4. The antibody of any one of claims 1, 2, or 3, wherein said antibody is labeled with a detectable label.

* * * * *